(12) United States Patent
Urbaniak et al.

(10) Patent No.: US 7,285,524 B1
(45) Date of Patent: Oct. 23, 2007

(54) ALLO AND AUTO-REACTIVE T-CELL EPITOPES

(75) Inventors: Stanislaw Joseph Urbaniak, Aberdeen (GB); Robert Norman Barker, Inverurie (GB)

(73) Assignees: Aberdeen University, Aberdeen (GB); Commom Services Agency for the Scottish Health Service, Edinburgh (GB)

( * ) Notice: Subject to any disclaimer, the term of this patent is extended or adjusted under 35 U.S.C. 154(b) by 0 days.

(21) Appl. No.: 09/857,097

(22) PCT Filed: Dec. 1, 1999

(86) PCT No.: PCT/GB99/04027

§ 371 (c)(1),
(2), (4) Date: Jul. 27, 2001

(87) PCT Pub. No.: WO00/32632

PCT Pub. Date: Jun. 8, 2000

(30) Foreign Application Priority Data

Dec. 1, 1998 (GB) .................................. 9826378.3

(51) Int. Cl.
*A61K 38/00* (2006.01)
*A61K 38/04* (2006.01)
*A61K 39/00* (2006.01)

(52) U.S. Cl. .................... 514/2; 424/184.1; 424/185.1; 424/810; 514/14

(58) Field of Classification Search ..................... None
See application file for complete search history.

(56) References Cited

OTHER PUBLICATIONS

Barker et al. Blood [1997] 90(7):2701-2715.*
Stott et al. Blood [1998] 92(10), part 1, supplement 1, p. 25A.*
VanderVegt, FP et al [1993] J. Exp. Med. 177:1587-1592.*

* cited by examiner

*Primary Examiner*—Christina Chan
*Assistant Examiner*—F. Pierre VanderVegt
(74) *Attorney, Agent, or Firm*—Licata & Tyrrell P.C.

(57) ABSTRACT

The present invention relates to a pharmaceutical composition for the prevention of alloimmunization of a subject or the immunosuppression of a response elicited by alloimmunization of a subject or an autoimmune haemolytic disease for said composition comprising an immunologically effective epitope of a rhesus protein or an immunologically active analogue or derivative thereof.

11 Claims, 6 Drawing Sheets

```
RHC:  MSSKYPRSVR RCLPLCALTL EAALILLFYF FTHYDASLED QKGLVASYQV    50
RHc:                        W
RHD:                        W

RHC:  GQDLTVMAAI GLGFLTSSFR RHSWSSVAFN LFMLALGVQW AILLDGFLSQ   100
RHc:              L          N
RHD:              I          S

RHC:  FPSGKVVITL FSIRLATMSA MSVLISAGAV LGKVNLAQLV VMVLVEVTAL   150
RHC:   P                         L       VD
RHD:   S

RHC:  GTLRMVISNI FNTDYHMNLR HFYVFAAYFG LTVAWCLPKP LPKGTEDNDQ   200
RHD:   N              MM   I                S              E

RHE:  RATIPSLSAM LGALFLWMFW PSVNSPLLRS PIQRKNAMFN TYYALAVSVV   250
RHe:                           I       F  A         E    V       V
RHD:   T

RHC:  TAISGSSLAH PQRKISMTYV HSAVLAGGVA VGTSCHLIPS PWLAMVLGLV   300
RHD:              G    K                   Y   G      PS I GY N

RHC:  AGLISGGAK  CLPVCCNRVL GIHHISVMHS IFSLLGLLGE ITYIVLLVLH   350
RHD:              V   Y G           PS I GY N              I        D

RHC:  TVWNGNGMIG FQVLLSIGEL SLAIVIALTS GLLTGLLLNL KIWKAPHVAK   400
RHD:   GA                                                          E

RHC:  YFDDQVFWKF PHLAVGF
RHD:
```

Figure 1

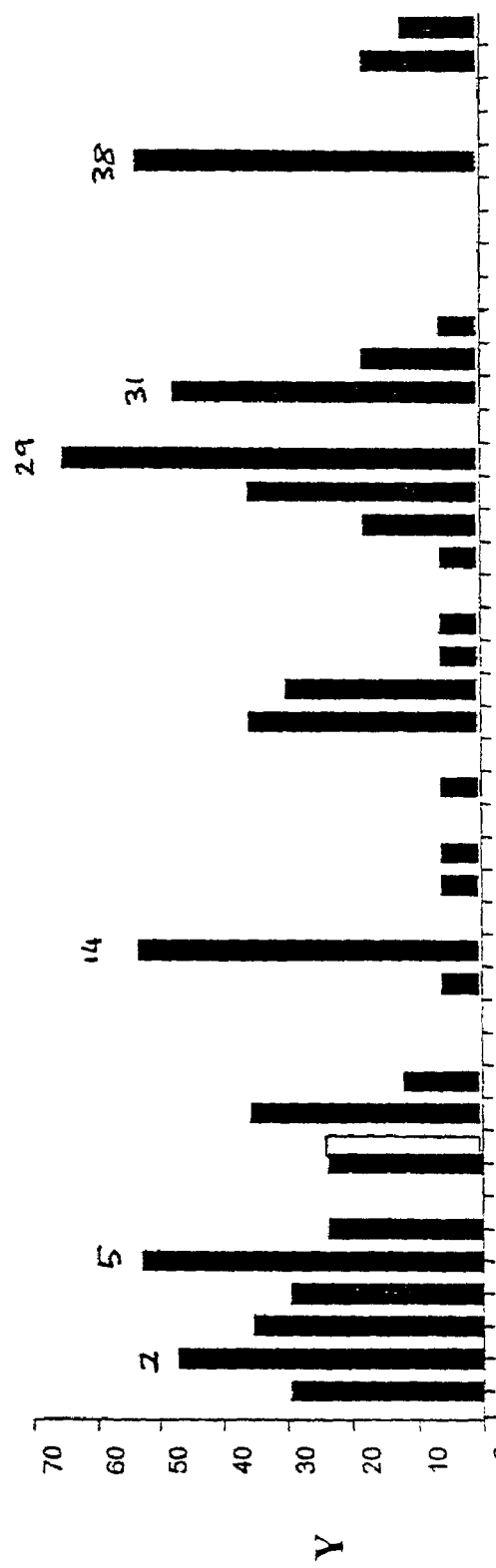
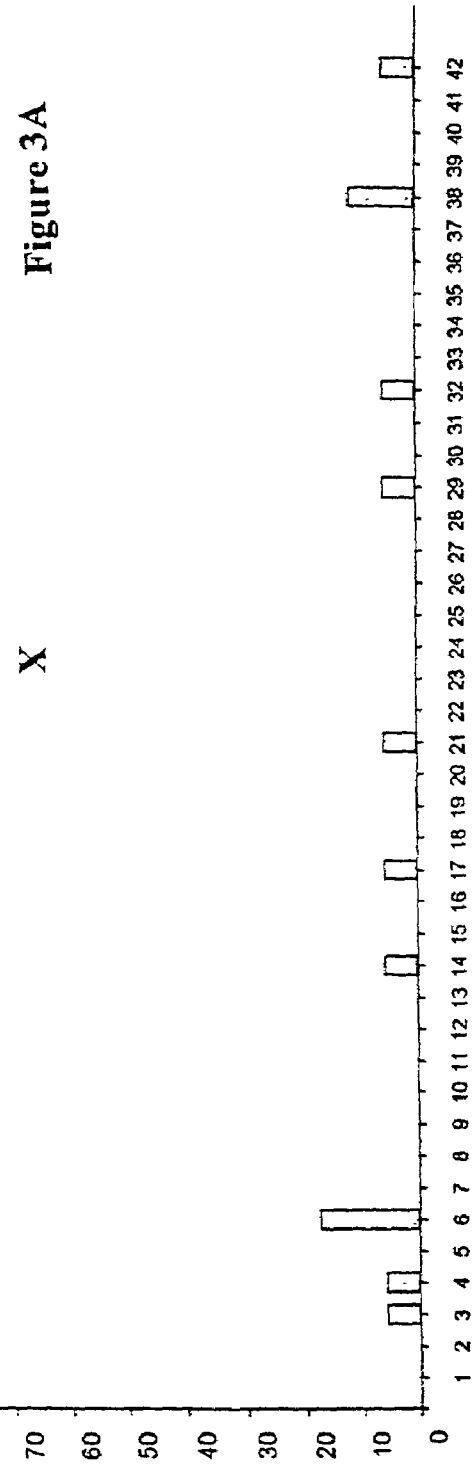
Figure 3A
Figure 3B

SEQUENCE LISTING

<160> NUMBER OF SEQ ID NOS: 152

<210> SEQ ID NO 1
<211> LENGTH: 15
<212> TYPE: PRT
<213> ORGANISM: Homo sapiens
<220> FEATURE:
<223> OTHER INFORMATION: Residues 2-16

<400> SEQUENCE: 1

Ser Ser Lys Tyr Pro Arg Ser Val Arg Arg Cys Leu Pro Leu Trp
 1               5                  10                  15

<210> SEQ ID NO 2
<211> LENGTH: 15
<212> TYPE: PRT
<213> ORGANISM: Homo sapiens
<220> FEATURE:
<223> OTHER INFORMATION: Residues 12-26

<400> SEQUENCE: 2

Cys Leu Pro Leu Trp Ala Leu Thr Leu Glu Ala Ala Leu Ile Leu
 1               5                  10                  15

<210> SEQ ID NO 3
<211> LENGTH: 15
<212> TYPE: PRT
<213> ORGANISM: Homo sapiens
<220> FEATURE:
<223> OTHER INFORMATION: RhCE (R2 CE) Residues 22-36

<400> SEQUENCE: 3

Ala Ala Leu Ile Leu Leu Phe Tyr Phe Phe Thr His Tyr Asp Ala
 1               5                  10                  15

<210> SEQ ID NO 4
<211> LENGTH: 15
<212> TYPE: PRT
<213> ORGANISM: Homo sapiens
<220> FEATURE:
<223> OTHER INFORMATION: RhCE (R2 CE) Residues 32-46

<400> SEQUENCE: 4

Thr His Tyr Asp Ala Ser Leu Glu Asp Gln Lys Gly Leu Val Ala
 1               5                  10                  15

<210> SEQ ID NO 5
<211> LENGTH: 15
<212> TYPE: PRT
<213> ORGANISM: Homo sapiens
<220> FEATURE:
<223> OTHER INFORMATION: RhCE (R2 CE) Residues 42-56

<400> SEQUENCE: 5

Lys Gly Leu Val Ala Ser Tyr Gln Val Gly Gln Asp Leu Thr Val
 1               5                  10                  15

<210> SEQ ID NO 6
<211> LENGTH: 15
<212> TYPE: PRT
<213> ORGANISM: Homo sapiens
<220> FEATURE:
<223> OTHER INFORMATION: RhCE (R2 CE) Residues 52-66

<400> SEQUENCE: 6

Gln Asp Leu Thr Val Met Ala Ala Leu Gly Leu Gly Phe Leu Thr
1               5                   10                  15

<210> SEQ ID NO 7
<211> LENGTH: 15
<212> TYPE: PRT
<213> ORGANISM: Homo sapiens
<220> FEATURE:
<223> OTHER INFORMATION: RhCE (R2 CE) Residues 62-76

<400> SEQUENCE: 7

Leu Gly Phe Leu Thr Ser Asn Phe Arg Arg His Ser Trp Ser Ser
1               5                   10                  15

<210> SEQ ID NO 8
<211> LENGTH: 15
<212> TYPE: PRT
<213> ORGANISM: Homo sapiens
<220> FEATURE:
<223> OTHER INFORMATION: RhCE (R2 CE) Residues 72-86

<400> SEQUENCE: 8

His Ser Trp Ser Ser Val Ala Phe Asn Leu Phe Met Leu Ala Leu
1               5                   10                  15

<210> SEQ ID NO 9
<211> LENGTH: 15
<212> TYPE: PRT
<213> ORGANISM: Homo sapiens
<220> FEATURE:
<223> OTHER INFORMATION: RhCE (R2 CE) Residues 82-96

<400> SEQUENCE: 9

Phe Met Leu Ala Leu Gly Val Gln Trp Ala Ile Leu Leu Asp Gly
1               5                   10                  15

<210> SEQ ID NO 10
<211> LENGTH: 15
<212> TYPE: PRT
<213> ORGANISM: Homo sapiens
<220> FEATURE:
<223> OTHER INFORMATION: RhCE (R2 CE) Residues 92-106

<400> SEQUENCE: 10

Ile Leu Leu Asp Gly Phe Leu Ser Gln Phe Pro Pro Gly Lys Val
1               5                   10                  15

<210> SEQ ID NO 11
<211> LENGTH: 15
<212> TYPE: PRT
<213> ORGANISM: Homo sapiens
<220> FEATURE:
<223> OTHER INFORMATION: RhCE (R2 CE) Residues 102-116

<400> SEQUENCE: 11

Pro Pro Gly Lys Val Val Ile Thr Leu Phe Ser Ile Arg Leu Ala
1               5                   10                  15

<210> SEQ ID NO 12
<211> LENGTH: 15
<212> TYPE: PRT
<213> ORGANISM: Homo sapiens
<220> FEATURE:
<223> OTHER INFORMATION: RhCE (R2 CE) Residues 112-126

<400> SEQUENCE: 12

Ser Ile Arg Leu Ala Thr Met Ser Ala Met Ser Val Leu Ile Ser

-continued

```
<210> SEQ ID NO 13
<211> LENGTH: 15
<212> TYPE: PRT
<213> ORGANISM: Homo sapiens
<220> FEATURE:
<223> OTHER INFORMATION: RhCE (R2 CE) Residues 122-136

<400> SEQUENCE: 13

Ser Val Leu Ile Ser Ala Gly Ala Val Leu Gly Lys Val Asn Leu
 1               5                  10                  15

<210> SEQ ID NO 14
<211> LENGTH: 15
<212> TYPE: PRT
<213> ORGANISM: Homo sapiens
<220> FEATURE:
<223> OTHER INFORMATION: RhCE (R2 CE) Residues 132-146

<400> SEQUENCE: 14

Gly Lys Val Asn Leu Ala Gln Leu Val Val Met Val Leu Val Glu
 1               5                  10                  15

<210> SEQ ID NO 15
<211> LENGTH: 15
<212> TYPE: PRT
<213> ORGANISM: Homo sapiens
<220> FEATURE:
<223> OTHER INFORMATION: RhCE (R2 CE) Residues 142-156

<400> SEQUENCE: 15

Met Val Leu Val Glu Val Thr Ala Leu Gly Thr Leu Arg Met Val
 1               5                  10                  15

<210> SEQ ID NO 16
<211> LENGTH: 15
<212> TYPE: PRT
<213> ORGANISM: Homo sapiens
<220> FEATURE:
<223> OTHER INFORMATION: RhCE (R2 CE) Residues 152-166

<400> SEQUENCE: 16

Thr Leu Arg Met Val Ile Ser Asn Ile Phe Asn Thr Asp Tyr His
 1               5                  10                  15

<210> SEQ ID NO 17
<211> LENGTH: 15
<212> TYPE: PRT
<213> ORGANISM: Homo sapiens
<220> FEATURE:
<223> OTHER INFORMATION: RhCE (R2 CE) Residues 162-176

<400> SEQUENCE: 17

Asn Thr Asp Tyr His Met Asn Leu Arg His Phe Tyr Val Phe Ala
 1               5                  10                  15

<210> SEQ ID NO 18
<211> LENGTH: 15
<212> TYPE: PRT
<213> ORGANISM: Homo sapiens
<220> FEATURE:
<223> OTHER INFORMATION: RhCE (R2 CE) Residues 172-186

<400> SEQUENCE: 18

Phe Tyr Val Phe Ala Ala Tyr Phe Gly Leu Thr Val Ala Trp Cys
 1               5                  10                  15
```

```
<210> SEQ ID NO 19
<211> LENGTH: 15
<212> TYPE: PRT
<213> ORGANISM: Homo sapiens
<220> FEATURE:
<223> OTHER INFORMATION: RhCE (R2 CE) Residues 182-196

<400> SEQUENCE: 19

Thr Val Ala Trp Cys Leu Pro Lys Pro Leu Pro Lys Gly Thr Glu
 1               5                  10                  15

<210> SEQ ID NO 20
<211> LENGTH: 15
<212> TYPE: PRT
<213> ORGANISM: Homo sapiens
<220> FEATURE:
<223> OTHER INFORMATION: RhCE (R2 CE) Residues 192-206

<400> SEQUENCE: 20

Pro Lys Gly Thr Glu Asp Asn Asp Gln Arg Ala Thr Ile Pro Ser
 1               5                  10                  15

<210> SEQ ID NO 21
<211> LENGTH: 15
<212> TYPE: PRT
<213> ORGANISM: Homo sapiens
<220> FEATURE:
<223> OTHER INFORMATION: RhCE (R2 CE) Residues 202-216

<400> SEQUENCE: 21

Ala Thr Ile Pro Ser Leu Ser Ala Met Leu Gly Ala Leu Phe Leu
 1               5                  10                  15

<210> SEQ ID NO 22
<211> LENGTH: 15
<212> TYPE: PRT
<213> ORGANISM: Homo sapiens
<220> FEATURE:
<223> OTHER INFORMATION: RhCE (R2 CE) Residues 212-226

<400> SEQUENCE: 22

Gly Ala Leu Phe Leu Trp Met Phe Trp Pro Ser Val Asn Ser Pro
 1               5                  10                  15

<210> SEQ ID NO 23
<211> LENGTH: 15
<212> TYPE: PRT
<213> ORGANISM: Homo sapiens
<220> FEATURE:
<223> OTHER INFORMATION: RhCE (R2 CE) Residues 222-236

<400> SEQUENCE: 23

Ser Val Asn Ser Pro Leu Leu Arg Ser Pro Ile Gln Arg Lys Asn
 1               5                  10                  15

<210> SEQ ID NO 24
<211> LENGTH: 15
<212> TYPE: PRT
<213> ORGANISM: Homo sapiens
<220> FEATURE:
<223> OTHER INFORMATION: RhCE (R2 CE) Residues 232-246

<400> SEQUENCE: 24

Ile Gln Arg Lys Asn Ala Met Phe Asn Thr Tyr Tyr Ala Leu Ala
 1               5                  10                  15
```

```
<210> SEQ ID NO 25
<211> LENGTH: 15
<212> TYPE: PRT
<213> ORGANISM: Homo sapiens
<220> FEATURE:
<223> OTHER INFORMATION: RhCE (R2 CE) Residues 242-256

<400> SEQUENCE: 25

Tyr Tyr Ala Leu Ala Val Ser Val Val Thr Ala Ile Ser Gly Ser
 1               5                  10                  15

<210> SEQ ID NO 26
<211> LENGTH: 15
<212> TYPE: PRT
<213> ORGANISM: Homo sapiens
<220> FEATURE:
<223> OTHER INFORMATION: RhCE (R2 CE) Residues 252-266

<400> SEQUENCE: 26

Ala Ile Ser Gly Ser Ser Leu Ala His Pro Gln Arg Lys Ile Ser
 1               5                  10                  15

<210> SEQ ID NO 27
<211> LENGTH: 15
<212> TYPE: PRT
<213> ORGANISM: Homo sapiens
<220> FEATURE:
<223> OTHER INFORMATION: RhCE (R2 CE) Residues 262-276

<400> SEQUENCE: 27

Gln Arg Lys Ile Ser Met Thr Tyr Val His Ser Ala Val Leu Ala
 1               5                  10                  15

<210> SEQ ID NO 28
<211> LENGTH: 15
<212> TYPE: PRT
<213> ORGANISM: Homo sapiens
<220> FEATURE:
<223> OTHER INFORMATION: RhCE (R2 CE) Residues 272-286

<400> SEQUENCE: 28

Ser Ala Val Leu Ala Gly Gly Val Ala Val Gly Thr Ser Cys His
 1               5                  10                  15

<210> SEQ ID NO 29
<211> LENGTH: 15
<212> TYPE: PRT
<213> ORGANISM: Homo sapiens
<220> FEATURE:
<223> OTHER INFORMATION: RhCE (R2 CE) Residues 282-296

<400> SEQUENCE: 29

Gly Thr Ser Cys His Leu Ile Pro Ser Pro Trp Leu Ala Met Val
 1               5                  10                  15

<210> SEQ ID NO 30
<211> LENGTH: 15
<212> TYPE: PRT
<213> ORGANISM: Homo sapiens
<220> FEATURE:
<223> OTHER INFORMATION: RhCE (R2 CE) Residues 292-306

<400> SEQUENCE: 30

Trp Leu Ala Met Val Leu Gly Leu Val Ala Gly Leu Ile Ser Ile
 1               5                  10                  15
```

```
<210> SEQ ID NO 31
<211> LENGTH: 15
<212> TYPE: PRT
<213> ORGANISM: Homo sapiens
<220> FEATURE:
<223> OTHER INFORMATION: RhCE (R2 CE) Residues 302-316

<400> SEQUENCE: 31

Gly Leu Ile Ser Ile Gly Gly Ala Lys Cys Leu Pro Val Cys Cys
 1               5                  10                  15

<210> SEQ ID NO 32
<211> LENGTH: 15
<212> TYPE: PRT
<213> ORGANISM: Homo sapiens
<220> FEATURE:
<223> OTHER INFORMATION: RhCE (R2 CE) Residues 312-326

<400> SEQUENCE: 32

Leu Pro Val Cys Cys Asn Arg Val Leu Gly Ile His His Ile Ser
 1               5                  10                  15

<210> SEQ ID NO 33
<211> LENGTH: 15
<212> TYPE: PRT
<213> ORGANISM: Homo sapiens
<220> FEATURE:
<223> OTHER INFORMATION: RhCE (R2 CE) Residues 322-336

<400> SEQUENCE: 33

Ile His His Ile Ser Val Met His Ser Ile Phe Ser Leu Leu Gly
 1               5                  10                  15

<210> SEQ ID NO 34
<211> LENGTH: 15
<212> TYPE: PRT
<213> ORGANISM: Homo sapiens
<220> FEATURE:
<223> OTHER INFORMATION: RhCE (R2 CE) Residues 332-346

<400> SEQUENCE: 34

Phe Ser Leu Leu Gly Leu Leu Gly Glu Ile Thr Tyr Ile Val Leu
 1               5                  10                  15

<210> SEQ ID NO 35
<211> LENGTH: 15
<212> TYPE: PRT
<213> ORGANISM: Homo sapiens
<220> FEATURE:
<223> OTHER INFORMATION: RhCE (R2 CE) Residues 342-356

<400> SEQUENCE: 35

Thr Tyr Ile Val Leu Leu Val Leu His Thr Val Trp Asn Gly Asn
 1               5                  10                  15

<210> SEQ ID NO 36
<211> LENGTH: 15
<212> TYPE: PRT
<213> ORGANISM: Homo sapiens
<220> FEATURE:
<223> OTHER INFORMATION: RhCE (R2 CE) Residues 352-366

<400> SEQUENCE: 36

Val Trp Asn Gly Asn Gly Met Ile Gly Phe Gln Val Leu Leu Ser
 1               5                  10                  15

<210> SEQ ID NO 37
```

```
<211> LENGTH: 15
<212> TYPE: PRT
<213> ORGANISM: Homo sapiens
<220> FEATURE:
<223> OTHER INFORMATION: RhCE (R2 CE) Residues 362-376

<400> SEQUENCE: 37

Gln Val Leu Leu Ser Ile Gly Glu Leu Ser Leu Ala Ile Val Ile
 1               5                  10                  15

<210> SEQ ID NO 38
<211> LENGTH: 15
<212> TYPE: PRT
<213> ORGANISM: Homo sapiens
<220> FEATURE:
<223> OTHER INFORMATION: RhCE (R2 CE) Residues 372-386

<400> SEQUENCE: 38

Leu Ala Ile Val Ile Ala Leu Thr Ser Gly Leu Leu Thr Gly Leu
 1               5                  10                  15

<210> SEQ ID NO 39
<211> LENGTH: 15
<212> TYPE: PRT
<213> ORGANISM: Homo sapiens
<220> FEATURE:
<223> OTHER INFORMATION: RhCE (R2 CE) Residues 382-396

<400> SEQUENCE: 39

Leu Leu Thr Gly Leu Leu Leu Asn Leu Lys Ile Trp Lys Ala Pro
 1               5                  10                  15

<210> SEQ ID NO 40
<211> LENGTH: 15
<212> TYPE: PRT
<213> ORGANISM: Homo sapiens
<220> FEATURE:
<223> OTHER INFORMATION: RhCE (R2 CE) Residues 392-406

<400> SEQUENCE: 40

Ile Trp Lys Ala Pro His Val Ala Lys Tyr Phe Asp Asp Gln Val
 1               5                  10                  15

<210> SEQ ID NO 41
<211> LENGTH: 15
<212> TYPE: PRT
<213> ORGANISM: Homo sapiens
<220> FEATURE:
<223> OTHER INFORMATION: RhCE (R2 cE) Residues 111-125

<400> SEQUENCE: 41

Phe Asp Asp Gln Val Phe Trp Lys Phe Pro His Leu Ala Val Gly
 1               5                  10                  15

<210> SEQ ID NO 42
<211> LENGTH: 15
<212> TYPE: PRT
<213> ORGANISM: Homo sapiens
<220> FEATURE:
<223> OTHER INFORMATION: RhCE (R2 cE) Residues 403-417

<400> SEQUENCE: 42

Asp Asp Gln Val Phe Trp Lys Phe Pro His Leu Ala Val Gly Phe
 1               5                  10                  15

<210> SEQ ID NO 43
<211> LENGTH: 15
```

```
<212> TYPE: PRT
<213> ORGANISM: Homo sapiens
<220> FEATURE:
<223> OTHER INFORMATION: RhCE (R1 Ce) Residues 2-16

<400> SEQUENCE: 43

Ser Ser Lys Tyr Pro Arg Ser Val Arg Arg Cys Leu Pro Leu Cys
  1               5                  10                  15

<210> SEQ ID NO 44
<211> LENGTH: 15
<212> TYPE: PRT
<213> ORGANISM: Homo sapiens
<220> FEATURE:
<223> OTHER INFORMATION: RhCE (R1 Ce) Residues 12-26

<400> SEQUENCE: 44

Cys Leu Pro Leu Cys Ala Leu Thr Leu Glu Ala Ala Leu Ile Leu
  1               5                  10                  15

<210> SEQ ID NO 45
<211> LENGTH: 15
<212> TYPE: PRT
<213> ORGANISM: Homo sapiens
<220> FEATURE:
<223> OTHER INFORMATION: RhCE (R1 Ce) Residues 212-226

<400> SEQUENCE: 45

Gly Ala Leu Phe Leu Trp Met Phe Trp Pro Ser Val Asn Ser Ala
  1               5                  10                  15

<210> SEQ ID NO 46
<211> LENGTH: 15
<212> TYPE: PRT
<213> ORGANISM: Homo sapiens
<220> FEATURE:
<223> OTHER INFORMATION: RhCE (R1 Ce) Residues 222-236

<400> SEQUENCE: 46

Ser Val Asn Ser Ala Leu Leu Arg Ser Pro Ile Gln Arg Lys Asn
  1               5                  10                  15

<210> SEQ ID NO 47
<211> LENGTH: 15
<212> TYPE: PRT
<213> ORGANISM: Homo sapiens
<220> FEATURE:
<223> OTHER INFORMATION: RhD Residues 52-66

<400> SEQUENCE: 47

Gln Asp Leu Thr Val Met Ala Ala Ile Gly Leu Gly Phe Leu Thr
  1               5                  10                  15

<210> SEQ ID NO 48
<211> LENGTH: 15
<212> TYPE: PRT
<213> ORGANISM: Homo sapiens
<220> FEATURE:
<223> OTHER INFORMATION: RhD Residues 62-76

<400> SEQUENCE: 48

Leu Gly Phe Leu Thr Ser Ser Phe Arg Arg His Ser Trp Ser Ser
  1               5                  10                  15

<210> SEQ ID NO 49
<211> LENGTH: 15
<212> TYPE: PRT
```

```
<213> ORGANISM: Homo sapiens
<220> FEATURE:
<223> OTHER INFORMATION: RhD Residues 92-106

<400> SEQUENCE: 49

Ile Leu Leu Asp Gly Phe Leu Ser Gln Phe Pro Ser Gly Lys Val
 1               5                  10                  15

<210> SEQ ID NO 50
<211> LENGTH: 15
<212> TYPE: PRT
<213> ORGANISM: Homo sapiens
<220> FEATURE:
<223> OTHER INFORMATION: RhD Residues 102-116

<400> SEQUENCE: 50

Pro Ser Gly Lys Val Val Ile Thr Leu Phe Ser Ile Arg Leu Ala
 1               5                  10                  15

<210> SEQ ID NO 51
<211> LENGTH: 15
<212> TYPE: PRT
<213> ORGANISM: Homo sapiens
<220> FEATURE:
<223> OTHER INFORMATION: RhD Residues 112-126

<400> SEQUENCE: 51

Ser Ile Arg Leu Ala Thr Met Ser Ala Leu Ser Val Leu Ile Ser
 1               5                  10                  15

<210> SEQ ID NO 52
<211> LENGTH: 15
<212> TYPE: PRT
<213> ORGANISM: Homo sapiens
<220> FEATURE:
<223> OTHER INFORMATION: RhD Residues 122-136

<400> SEQUENCE: 52

Ser Val Leu Ile Ser Val Asp Ala Val Leu Gly Lys Val Asn Leu
 1               5                  10                  15

<210> SEQ ID NO 53
<211> LENGTH: 15
<212> TYPE: PRT
<213> ORGANISM: Homo sapiens
<220> FEATURE:
<223> OTHER INFORMATION: RhD Residues 142-156

<400> SEQUENCE: 53

Met Val Leu Val Glu Val Thr Ala Leu Gly Asn Leu Arg Met Val
 1               5                  10                  15

<210> SEQ ID NO 54
<211> LENGTH: 15
<212> TYPE: PRT
<213> ORGANISM: Homo sapiens
<220> FEATURE:
<223> OTHER INFORMATION: RhD Residues 152-166

<400> SEQUENCE: 54

Asn Leu Arg Met Val Ile Ser Asn Ile Phe Asn Thr Asp Tyr His
 1               5                  10                  15

<210> SEQ ID NO 55
<211> LENGTH: 15
<212> TYPE: PRT
<213> ORGANISM: Homo sapiens
```

```
<220> FEATURE:
<223> OTHER INFORMATION: RhD Residues 162-176

<400> SEQUENCE: 55

Asn Thr Asp Tyr His Met Asn Met Met His Ile Tyr Val Phe Ala
 1               5                  10                  15

<210> SEQ ID NO 56
<211> LENGTH: 15
<212> TYPE: PRT
<213> ORGANISM: Homo sapiens
<220> FEATURE:
<223> OTHER INFORMATION: RhD Residues 172-186

<400> SEQUENCE: 56

Ile Tyr Val Phe Ala Ala Tyr Phe Gly Leu Ser Val Ala Trp Cys
 1               5                  10                  15

<210> SEQ ID NO 57
<211> LENGTH: 15
<212> TYPE: PRT
<213> ORGANISM: Homo sapiens
<220> FEATURE:
<223> OTHER INFORMATION: RhD Residues 182-196

<400> SEQUENCE: 57

Ser Val Ala Trp Cys Leu Pro Lys Pro Leu Pro Glu Gly Thr Glu
 1               5                  10                  15

<210> SEQ ID NO 58
<211> LENGTH: 15
<212> TYPE: PRT
<213> ORGANISM: Homo sapiens
<220> FEATURE:
<223> OTHER INFORMATION: RhD Residues 192-206

<400> SEQUENCE: 58

Pro Glu Gly Thr Glu Asp Lys Asp Gln Thr Ala Thr Ile Pro Ser
 1               5                  10                  15

<210> SEQ ID NO 59
<211> LENGTH: 15
<212> TYPE: PRT
<213> ORGANISM: Homo sapiens
<220> FEATURE:
<223> OTHER INFORMATION: RhD Residues 212-226

<400> SEQUENCE: 59

Gly Ala Leu Phe Leu Trp Ile Phe Trp Pro Ser Phe Asn Ser Ala
 1               5                  10                  15

<210> SEQ ID NO 60
<211> LENGTH: 15
<212> TYPE: PRT
<213> ORGANISM: Homo sapiens
<220> FEATURE:
<223> OTHER INFORMATION: RhD Residues 222-236

<400> SEQUENCE: 60

Ser Phe Asn Ser Ala Leu Leu Arg Ser Pro Ile Glu Arg Lys Asn
 1               5                  10                  15

<210> SEQ ID NO 61
<211> LENGTH: 15
<212> TYPE: PRT
<213> ORGANISM: Homo sapiens
<220> FEATURE:
```

-continued

<223> OTHER INFORMATION: RhD Residues 232-246

<400> SEQUENCE: 61

Ile Glu Arg Lys Asn Ala Val Phe Asn Thr Tyr Tyr Ala Val Ala
 1               5                  10                  15

<210> SEQ ID NO 62
<211> LENGTH: 15
<212> TYPE: PRT
<213> ORGANISM: Homo sapiens
<220> FEATURE:
<223> OTHER INFORMATION: RhD Residues 242-256

<400> SEQUENCE: 62

Tyr Tyr Ala Val Ala Val Ser Val Val Thr Ala Ile Ser Gly Ser
 1               5                  10                  15

<210> SEQ ID NO 63
<211> LENGTH: 15
<212> TYPE: PRT
<213> ORGANISM: Homo sapiens
<220> FEATURE:
<223> OTHER INFORMATION: RhD Residues 252-266

<400> SEQUENCE: 63

Ala Ile Ser Gly Ser Ser Leu Ala His Pro Gln Gly Lys Ile Ser
 1               5                  10                  15

<210> SEQ ID NO 64
<211> LENGTH: 15
<212> TYPE: PRT
<213> ORGANISM: Homo sapiens
<220> FEATURE:
<223> OTHER INFORMATION: RhD Residues 262-276

<400> SEQUENCE: 64

Gln Gly Lys Ile Ser Lys Thr Tyr Val His Ser Ala Val Leu Ala
 1               5                  10                  15

<210> SEQ ID NO 65
<211> LENGTH: 15
<212> TYPE: PRT
<213> ORGANISM: Homo sapiens
<220> FEATURE:
<223> OTHER INFORMATION: RhD Residues 292-306

<400> SEQUENCE: 65

Trp Leu Ala Met Val Leu Gly Leu Val Ala Gly Leu Ile Ser Val
 1               5                  10                  15

<210> SEQ ID NO 66
<211> LENGTH: 15
<212> TYPE: PRT
<213> ORGANISM: Homo sapiens
<220> FEATURE:
<223> OTHER INFORMATION: RhD Residues 302-316

<400> SEQUENCE: 66

Gly Leu Ile Ser Val Gly Gly Ala Lys Tyr Leu Pro Gly Cys Cys
 1               5                  10                  15

<210> SEQ ID NO 67
<211> LENGTH: 15
<212> TYPE: PRT
<213> ORGANISM: Homo sapiens
<220> FEATURE:
<223> OTHER INFORMATION: RhD Residues 312-326

-continued

```
<400> SEQUENCE: 67

Leu Pro Gly Cys Cys Asn Arg Val Leu Gly Ile Pro His Ser Ser
 1               5                  10                  15

<210> SEQ ID NO 68
<211> LENGTH: 15
<212> TYPE: PRT
<213> ORGANISM: Homo sapiens
<220> FEATURE:
<223> OTHER INFORMATION: RhD Residues 322-336

<400> SEQUENCE: 68

Ile Pro His Ser Ser Ile Met Gly Tyr Asn Phe Ser Leu Leu Gly
 1               5                  10                  15

<210> SEQ ID NO 69
<211> LENGTH: 15
<212> TYPE: PRT
<213> ORGANISM: Homo sapiens
<220> FEATURE:
<223> OTHER INFORMATION: RhD Residues 332-346

<400> SEQUENCE: 69

Phe Ser Leu Leu Gly Leu Leu Gly Glu Ile Ile Tyr Ile Val Leu
 1               5                  10                  15

<210> SEQ ID NO 70
<211> LENGTH: 15
<212> TYPE: PRT
<213> ORGANISM: Homo sapiens
<220> FEATURE:
<223> OTHER INFORMATION: RhD Residues 342-356

<400> SEQUENCE: 70

Ile Tyr Ile Val Leu Leu Val Leu Asp Thr Val Gly Ala Gly Asn
 1               5                  10                  15

<210> SEQ ID NO 71
<211> LENGTH: 15
<212> TYPE: PRT
<213> ORGANISM: Homo sapiens
<220> FEATURE:
<223> OTHER INFORMATION: RhD Residues 352-366

<400> SEQUENCE: 71

Val Gly Ala Gly Asn Gly Met Ile Gly Phe Gln Val Leu Leu Ser
 1               5                  10                  15

<210> SEQ ID NO 72
<211> LENGTH: 15
<212> TYPE: PRT
<213> ORGANISM: Homo sapiens
<220> FEATURE:
<223> OTHER INFORMATION: RhD Residues 392-406

<400> SEQUENCE: 72

Ile Trp Lys Ala Pro His Glu Ala Lys Tyr Phe Asp Asp Gln Val
 1               5                  10                  15

<210> SEQ ID NO 73
<211> LENGTH: 15
<212> TYPE: PRT
<213> ORGANISM: Homo sapiens
<220> FEATURE:
<223> OTHER INFORMATION: RhCE (R1 Ce) Residues 7-21
```

```
<400> SEQUENCE: 73

Arg Ser Val Arg Arg Cys Leu Pro Leu Cys Ala Leu Thr Leu Glu
  1               5                  10                  15

<210> SEQ ID NO 74
<211> LENGTH: 15
<212> TYPE: PRT
<213> ORGANISM: Homo sapiens
<220> FEATURE:
<223> OTHER INFORMATION: RhCE (R1 Ce) Residues 217-231

<400> SEQUENCE: 74

Trp Met Phe Trp Pro Ser Val Asn Ser Ala Leu Leu Arg Ser Pro
  1               5                  10                  15

<210> SEQ ID NO 75
<211> LENGTH: 15
<212> TYPE: PRT
<213> ORGANISM: Homo sapiens
<220> FEATURE:
<223> OTHER INFORMATION: RhD Residues 57-71

<400> SEQUENCE: 75

Met Ala Ala Ile Gly Leu Gly Phe Leu Thr Ser Ser Phe Arg Arg
  1               5                  10                  15

<210> SEQ ID NO 76
<211> LENGTH: 15
<212> TYPE: PRT
<213> ORGANISM: Homo sapiens
<220> FEATURE:
<223> OTHER INFORMATION: RhD Residues 67-81

<400> SEQUENCE: 76

Ser Ser Phe Arg Arg His Ser Trp Ser Ser Val Ala Phe Asn Leu
  1               5                  10                  15

<210> SEQ ID NO 77
<211> LENGTH: 15
<212> TYPE: PRT
<213> ORGANISM: Homo sapiens
<220> FEATURE:
<223> OTHER INFORMATION: RhD Residues 97-111

<400> SEQUENCE: 77

Phe Leu Ser Gln Phe Pro Ser Gly Lys Val Val Ile Thr Leu Phe
  1               5                  10                  15

<210> SEQ ID NO 78
<211> LENGTH: 15
<212> TYPE: PRT
<213> ORGANISM: Homo sapiens
<220> FEATURE:
<223> OTHER INFORMATION: RhD Residues 107-121

<400> SEQUENCE: 78

Val Ile Thr Leu Phe Ser Ile Arg Leu Ala Thr Met Ser Ala Leu
  1               5                  10                  15

<210> SEQ ID NO 79
<211> LENGTH: 15
<212> TYPE: PRT
<213> ORGANISM: Homo sapiens
<220> FEATURE:
<223> OTHER INFORMATION: RhD Residues 117-131

<400> SEQUENCE: 79
```

Thr Met Ser Ala Leu Ser Val Leu Ile Ser Val Asp Ala Val Leu
 1               5                  10                  15

<210> SEQ ID NO 80
<211> LENGTH: 15
<212> TYPE: PRT
<213> ORGANISM: Homo sapiens
<220> FEATURE:
<223> OTHER INFORMATION: RhD Residues 127-141

<400> SEQUENCE: 80

Val Asp Ala Val Leu Gly Lys Val Asn Leu Ala Gln Leu Val Val
 1               5                  10                  15

<210> SEQ ID NO 81
<211> LENGTH: 15
<212> TYPE: PRT
<213> ORGANISM: Homo sapiens
<220> FEATURE:
<223> OTHER INFORMATION: RhD Residues 147-161

<400> SEQUENCE: 81

Val Thr Ala Leu Gly Asn Leu Arg Met Val Ile Ser Asn Ile Phe
 1               5                  10                  15

<210> SEQ ID NO 82
<211> LENGTH: 15
<212> TYPE: PRT
<213> ORGANISM: Homo sapiens
<220> FEATURE:
<223> OTHER INFORMATION: RhD Residues 157-171

<400> SEQUENCE: 82

Ile Ser Asn Ile Phe Asn Thr Asp Tyr His Met Asn Met Met His
 1               5                  10                  15

<210> SEQ ID NO 83
<211> LENGTH: 15
<212> TYPE: PRT
<213> ORGANISM: Homo sapiens
<220> FEATURE:
<223> OTHER INFORMATION: RhD Residues 167-181

<400> SEQUENCE: 83

Met Asn Met Met His Ile Tyr Val Phe Ala Ala Tyr Phe Gly Leu
 1               5                  10                  15

<210> SEQ ID NO 84
<211> LENGTH: 15
<212> TYPE: PRT
<213> ORGANISM: Homo sapiens
<220> FEATURE:
<223> OTHER INFORMATION: RhD Residues 177-191

<400> SEQUENCE: 84

Ala Tyr Phe Gly Leu Ser Val Ala Trp Cys Leu Pro Lys Pro Leu
 1               5                  10                  15

<210> SEQ ID NO 85
<211> LENGTH: 15
<212> TYPE: PRT
<213> ORGANISM: Homo sapiens
<220> FEATURE:
<223> OTHER INFORMATION: RhD Residues 187-201

<400> SEQUENCE: 85

Leu Pro Lys Pro Leu Pro Glu Gly Thr Glu Asp Lys Asp Gln Thr
 1               5                  10                  15

<210> SEQ ID NO 86
<211> LENGTH: 15
<212> TYPE: PRT
<213> ORGANISM: Homo sapiens
<220> FEATURE:
<223> OTHER INFORMATION: RhD Residues 197-211

<400> SEQUENCE: 86

Asp Lys Asp Gln Thr Ala Thr Ile Pro Ser Leu Ser Ala Met Leu
 1               5                  10                  15

<210> SEQ ID NO 87
<211> LENGTH: 15
<212> TYPE: PRT
<213> ORGANISM: Homo sapiens
<220> FEATURE:
<223> OTHER INFORMATION: RhD Residues 207-221

<400> SEQUENCE: 87

Leu Ser Ala Met Leu Gly Ala Leu Phe Leu Trp Ile Phe Trp Pro
 1               5                  10                  15

<210> SEQ ID NO 88
<211> LENGTH: 15
<212> TYPE: PRT
<213> ORGANISM: Homo sapiens
<220> FEATURE:
<223> OTHER INFORMATION: RhD Residues 217-231

<400> SEQUENCE: 88

Trp Ile Phe Trp Pro Ser Phe Asn Ser Ala Leu Leu Arg Ser Pro
 1               5                  10                  15

<210> SEQ ID NO 89
<211> LENGTH: 15
<212> TYPE: PRT
<213> ORGANISM: Homo sapiens
<220> FEATURE:
<223> OTHER INFORMATION: RhD Residues 227-241

<400> SEQUENCE: 89

Leu Leu Arg Ser Pro Ile Glu Arg Lys Asn Ala Val Phe Asn Thr
 1               5                  10                  15

<210> SEQ ID NO 90
<211> LENGTH: 15
<212> TYPE: PRT
<213> ORGANISM: Homo sapiens
<220> FEATURE:
<223> OTHER INFORMATION: RhD Residues 237-251

<400> SEQUENCE: 90

Ala Val Phe Asn Thr Tyr Tyr Ala Val Ala Val Ser Val Val Thr
 1               5                  10                  15

<210> SEQ ID NO 91
<211> LENGTH: 15
<212> TYPE: PRT
<213> ORGANISM: Homo sapiens
<220> FEATURE:
<223> OTHER INFORMATION: RhD Residues 257-271

<400> SEQUENCE: 91

Ser Leu Ala His Pro Gln Gly Lys Ile Ser Lys Thr Tyr Val His

-continued

<210> SEQ ID NO 92
<211> LENGTH: 15
<212> TYPE: PRT
<213> ORGANISM: Homo sapiens
<220> FEATURE:
<223> OTHER INFORMATION: RhD Residues 267-281

<400> SEQUENCE: 92

Lys Thr Tyr Val His Ser Ala Val Leu Ala Gly Gly Val Ala Val
 1               5                  10                  15

<210> SEQ ID NO 93
<211> LENGTH: 15
<212> TYPE: PRT
<213> ORGANISM: Homo sapiens
<220> FEATURE:
<223> OTHER INFORMATION: RhD Residues 297-311

<400> SEQUENCE: 93

Leu Gly Leu Val Ala Gly Leu Ile Ser Val Gly Gly Ala Lys Tyr
 1               5                  10                  15

<210> SEQ ID NO 94
<211> LENGTH: 15
<212> TYPE: PRT
<213> ORGANISM: Homo sapiens
<220> FEATURE:
<223> OTHER INFORMATION: RhD Residues 307-321

<400> SEQUENCE: 94

Gly Gly Ala Lys Tyr Leu Pro Gly Cys Cys Asn Arg Val Leu Gly
 1               5                  10                  15

<210> SEQ ID NO 95
<211> LENGTH: 15
<212> TYPE: PRT
<213> ORGANISM: Homo sapiens
<220> FEATURE:
<223> OTHER INFORMATION: RhD Residues 317-331

<400> SEQUENCE: 95

Asn Arg Val Leu Gly Ile Pro His Ser Ser Ile Met Gly Tyr Asn
 1               5                  10                  15

<210> SEQ ID NO 96
<211> LENGTH: 15
<212> TYPE: PRT
<213> ORGANISM: Homo sapiens
<220> FEATURE:
<223> OTHER INFORMATION: RhD Residues 327-341

<400> SEQUENCE: 96

Ile Met Gly Tyr Asn Phe Ser Leu Leu Gly Leu Leu Gly Glu Ile
 1               5                  10                  15

<210> SEQ ID NO 97
<211> LENGTH: 15
<212> TYPE: PRT
<213> ORGANISM: Homo sapiens
<220> FEATURE:
<223> OTHER INFORMATION: RhD Residues 337-351

<400> SEQUENCE: 97

Leu Leu Gly Glu Ile Ile Tyr Ile Val Leu Leu Val Leu Asp Thr
 1               5                  10                  15

```
<210> SEQ ID NO 98
<211> LENGTH: 15
<212> TYPE: PRT
<213> ORGANISM: Homo sapiens
<220> FEATURE:
<223> OTHER INFORMATION: RhD Residues 347-361

<400> SEQUENCE: 98

Leu Val Leu Asp Thr Val Gly Ala Gly Asn Gly Met Ile Gly Phe
 1               5                  10                  15

<210> SEQ ID NO 99
<211> LENGTH: 15
<212> TYPE: PRT
<213> ORGANISM: Homo sapiens
<220> FEATURE:
<223> OTHER INFORMATION: RhD Residues 387-401

<400> SEQUENCE: 99

Leu Leu Asn Leu Lys Ile Trp Lys Ala Pro His Glu Ala Lys Tyr
 1               5                  10                  15

<210> SEQ ID NO 100
<211> LENGTH: 15
<212> TYPE: PRT
<213> ORGANISM: Homo sapiens
<220> FEATURE:
<223> OTHER INFORMATION: RhD Residues 397-411

<400> SEQUENCE: 100

His Glu Ala Lys Tyr Phe Asp Asp Gln Val Phe Trp Lys Phe Pro
 1               5                  10                  15

<210> SEQ ID NO 101
<211> LENGTH: 15
<212> TYPE: PRT
<213> ORGANISM: Homo sapiens
<220> FEATURE:
<223> OTHER INFORMATION: Rh50 GP Residues 1-15

<400> SEQUENCE: 101

Met Arg Phe Thr Phe Pro Leu Met Ala Ile Val Leu Glu Ile Ala
 1               5                  10                  15

<210> SEQ ID NO 102
<211> LENGTH: 15
<212> TYPE: PRT
<213> ORGANISM: Homo sapiens
<220> FEATURE:
<223> OTHER INFORMATION: Rh50 GP Residues 11-25

<400> SEQUENCE: 102

Val Leu Glu Ile Ala Met Ile Val Leu Phe Gly Leu Phe Val Glu
 1               5                  10                  15

<210> SEQ ID NO 103
<211> LENGTH: 15
<212> TYPE: PRT
<213> ORGANISM: Homo sapiens
<220> FEATURE:
<223> OTHER INFORMATION: Rh50 GP Residues 21-35

<400> SEQUENCE: 103

Gly Leu Phe Val Glu Tyr Glu Thr Asp Gln Thr Val Leu Glu Gln
 1               5                  10                  15
```

-continued

<210> SEQ ID NO 104
<211> LENGTH: 15
<212> TYPE: PRT
<213> ORGANISM: Homo sapiens
<220> FEATURE:
<223> OTHER INFORMATION: Rh50 GP Residues 31-45

<400> SEQUENCE: 104

Thr Val Leu Glu Gln Leu Asn Ile Thr Lys Pro Thr Asp Met Gly
 1               5                  10                  15

<210> SEQ ID NO 105
<211> LENGTH: 15
<212> TYPE: PRT
<213> ORGANISM: Homo sapiens
<220> FEATURE:
<223> OTHER INFORMATION: Rh50 GP Residues 41-55

<400> SEQUENCE: 105

Pro Thr Asp Met Gly Ile Phe Phe Glu Leu Tyr Pro Leu Phe Gln
 1               5                  10                  15

<210> SEQ ID NO 106
<211> LENGTH: 15
<212> TYPE: PRT
<213> ORGANISM: Homo sapiens
<220> FEATURE:
<223> OTHER INFORMATION: Rh50 GP Residues 51-65

<400> SEQUENCE: 106

Tyr Pro Leu Phe Gln Asp Val His Val Met Ile Phe Val Gly Phe
 1               5                  10                  15

<210> SEQ ID NO 107
<211> LENGTH: 15
<212> TYPE: PRT
<213> ORGANISM: Homo sapiens
<220> FEATURE:
<223> OTHER INFORMATION: Rh50 GP Residues 61-75

<400> SEQUENCE: 107

Ile Phe Val Gly Phe Gly Phe Leu Met Thr Phe Leu Lys Lys Tyr
 1               5                  10                  15

<210> SEQ ID NO 108
<211> LENGTH: 15
<212> TYPE: PRT
<213> ORGANISM: Homo sapiens
<220> FEATURE:
<223> OTHER INFORMATION: Rh50 GP Residues 71-85

<400> SEQUENCE: 108

Phe Leu Lys Lys Tyr Gly Phe Ser Ser Val Gly Ile Asn Leu Leu
 1               5                  10                  15

<210> SEQ ID NO 109
<211> LENGTH: 15
<212> TYPE: PRT
<213> ORGANISM: Homo sapiens
<220> FEATURE:
<223> OTHER INFORMATION: Rh50 GP Residues 81-95

<400> SEQUENCE: 109

Gly Ile Asn Leu Leu Val Ala Ala Leu Gly Leu Gln Trp Gly Thr
 1               5                  10                  15

-continued

<210> SEQ ID NO 110
<211> LENGTH: 15
<212> TYPE: PRT
<213> ORGANISM: Homo sapiens
<220> FEATURE:
<223> OTHER INFORMATION: Rh50 GP Residues 91-105

<400> SEQUENCE: 110

Leu Gln Trp Gly Thr Ile Val Gln Gly Ile Leu Gln Ser Gln Gly
 1               5                  10                  15

<210> SEQ ID NO 111
<211> LENGTH: 15
<212> TYPE: PRT
<213> ORGANISM: Homo sapiens
<220> FEATURE:
<223> OTHER INFORMATION: Rh50 GP Residues 101-115

<400> SEQUENCE: 111

Leu Gln Ser Gln Gly Gln Lys Phe Asn Ile Gly Ile Lys Asn Met
 1               5                  10                  15

<210> SEQ ID NO 112
<211> LENGTH: 15
<212> TYPE: PRT
<213> ORGANISM: Homo sapiens
<220> FEATURE:
<223> OTHER INFORMATION: Rh50 GP Residues 111-125

<400> SEQUENCE: 112

Gly Ile Lys Asn Met Ile Asn Ala Asp Phe Ser Ala Ala Thr Val
 1               5                  10                  15

<210> SEQ ID NO 113
<211> LENGTH: 15
<212> TYPE: PRT
<213> ORGANISM: Homo sapiens
<220> FEATURE:
<223> OTHER INFORMATION: Rh50 GP Residues 121-135

<400> SEQUENCE: 113

Ser Ala Ala Thr Val Leu Ile Ser Phe Gly Ala Val Leu Gly Lys
 1               5                  10                  15

<210> SEQ ID NO 114
<211> LENGTH: 15
<212> TYPE: PRT
<213> ORGANISM: Homo sapiens
<220> FEATURE:
<223> OTHER INFORMATION: Rh50 GP Residues 131-145

<400> SEQUENCE: 114

Ala Val Leu Gly Lys Thr Ser Pro Thr Gln Met Leu Ile Met Thr
 1               5                  10                  15

<210> SEQ ID NO 115
<211> LENGTH: 15
<212> TYPE: PRT
<213> ORGANISM: Homo sapiens
<220> FEATURE:
<223> OTHER INFORMATION: Rh50 GP Residues 141-155

<400> SEQUENCE: 115

Met Leu Ile Met Thr Ile Leu Glu Ile Val Phe Phe Ala His Asn
 1               5                  10                  15

<210> SEQ ID NO 116

-continued

```
<211> LENGTH: 15
<212> TYPE: PRT
<213> ORGANISM: Homo sapiens
<220> FEATURE:
<223> OTHER INFORMATION: Rh50 GP Residues 151-165

<400> SEQUENCE: 116

Phe Phe Ala His Asn Glu Tyr Leu Val Ser Glu Ile Phe Lys Ala
 1               5                  10                  15

<210> SEQ ID NO 117
<211> LENGTH: 15
<212> TYPE: PRT
<213> ORGANISM: Homo sapiens
<220> FEATURE:
<223> OTHER INFORMATION: Rh50 GP Residues 161-175

<400> SEQUENCE: 117

Glu Ile Phe Lys Ala Ser Asp Ile Gly Ala Ser Met Thr Ile His
 1               5                  10                  15

<210> SEQ ID NO 118
<211> LENGTH: 15
<212> TYPE: PRT
<213> ORGANISM: Homo sapiens
<220> FEATURE:
<223> OTHER INFORMATION: Rh50 GP Residues 171-185

<400> SEQUENCE: 118

Ser Met Thr Ile His Ala Phe Gly Ala Tyr Phe Gly Leu Ala Val
 1               5                  10                  15

<210> SEQ ID NO 119
<211> LENGTH: 15
<212> TYPE: PRT
<213> ORGANISM: Homo sapiens
<220> FEATURE:
<223> OTHER INFORMATION: Rh50 GP Residues 181-195

<400> SEQUENCE: 119

Phe Gly Leu Ala Val Ala Gly Ile Leu Tyr Arg Ser Gly Leu Arg
 1               5                  10                  15

<210> SEQ ID NO 120
<211> LENGTH: 15
<212> TYPE: PRT
<213> ORGANISM: Homo sapiens
<220> FEATURE:
<223> OTHER INFORMATION: Rh50 GP Residues 191-205

<400> SEQUENCE: 120

Arg Ser Gly Leu Arg Lys Gly His Glu Asn Glu Glu Ser Ala Tyr
 1               5                  10                  15

<210> SEQ ID NO 121
<211> LENGTH: 15
<212> TYPE: PRT
<213> ORGANISM: Homo sapiens
<220> FEATURE:
<223> OTHER INFORMATION: Rh50 GP Residues 201-215

<400> SEQUENCE: 121

Glu Glu Ser Ala Tyr Tyr Ser Asp Leu Phe Ala Met Ile Gly Thr
 1               5                  10                  15

<210> SEQ ID NO 122
<211> LENGTH: 15
```

```
<212> TYPE: PRT
<213> ORGANISM: Homo sapiens
<220> FEATURE:
<223> OTHER INFORMATION: Rh50 GP Residues 211-225

<400> SEQUENCE: 122

Ala Met Ile Gly Thr Leu Phe Leu Trp Met Phe Trp Pro Ser Phe
 1               5                  10                  15

<210> SEQ ID NO 123
<211> LENGTH: 15
<212> TYPE: PRT
<213> ORGANISM: Homo sapiens
<220> FEATURE:
<223> OTHER INFORMATION: Rh50 GP Residues 221-235

<400> SEQUENCE: 123

Phe Trp Pro Ser Phe Asn Ser Ala Ile Ala Glu Pro Gly Asp Lys
 1               5                  10                  15

<210> SEQ ID NO 124
<211> LENGTH: 15
<212> TYPE: PRT
<213> ORGANISM: Homo sapiens
<220> FEATURE:
<223> OTHER INFORMATION: Rh50 GP Residues 231-245

<400> SEQUENCE: 124

Glu Pro Gly Asp Lys Gln Cys Arg Ala Ile Val Asp Thr Tyr Phe
 1               5                  10                  15

<210> SEQ ID NO 125
<211> LENGTH: 15
<212> TYPE: PRT
<213> ORGANISM: Homo sapiens
<220> FEATURE:
<223> OTHER INFORMATION: Rh50 GP Residues 241-255

<400> SEQUENCE: 125

Val Asp Thr Tyr Phe Ser Leu Ala Ala Cys Val Leu Thr Ala Phe
 1               5                  10                  15

<210> SEQ ID NO 126
<211> LENGTH: 15
<212> TYPE: PRT
<213> ORGANISM: Homo sapiens
<220> FEATURE:
<223> OTHER INFORMATION: Rh50 GP Residues 251-265

<400> SEQUENCE: 126

Val Leu Thr Ala Phe Ala Phe Ser Ser Leu Val Glu His Arg Gly
 1               5                  10                  15

<210> SEQ ID NO 127
<211> LENGTH: 15
<212> TYPE: PRT
<213> ORGANISM: Homo sapiens
<220> FEATURE:
<223> OTHER INFORMATION: Rh50 GP Residues 261-275

<400> SEQUENCE: 127

Val Glu His Arg Gly Lys Leu Asn Met Val His Ile Gln Asn Ala
 1               5                  10                  15

<210> SEQ ID NO 128
<211> LENGTH: 15
<212> TYPE: PRT
```

```
<213> ORGANISM: Homo sapiens
<220> FEATURE:
<223> OTHER INFORMATION: Rh50 GP Residues 271-285

<400> SEQUENCE: 128

His Ile Gln Asn Ala Thr Leu Ala Gly Gly Val Ala Val Gly Thr
 1               5                  10                  15

<210> SEQ ID NO 129
<211> LENGTH: 15
<212> TYPE: PRT
<213> ORGANISM: Homo sapiens
<220> FEATURE:
<223> OTHER INFORMATION: Rh50 GP Residues 281-295

<400> SEQUENCE: 129

Val Ala Val Gly Thr Cys Ala Asp Met Ala Ile His Pro Phe Gly
 1               5                  10                  15

<210> SEQ ID NO 130
<211> LENGTH: 15
<212> TYPE: PRT
<213> ORGANISM: Homo sapiens
<220> FEATURE:
<223> OTHER INFORMATION: Rh50 GP Residues 291-305

<400> SEQUENCE: 130

Ile His Pro Phe Gly Ser Met Ile Ile Gly Ser Ile Ala Gly Met
 1               5                  10                  15

<210> SEQ ID NO 131
<211> LENGTH: 15
<212> TYPE: PRT
<213> ORGANISM: Homo sapiens
<220> FEATURE:
<223> OTHER INFORMATION: Rh50 GP Residues 301-315

<400> SEQUENCE: 131

Ser Ile Ala Gly Met Val Ser Val Leu Gly Tyr Lys Phe Leu Thr
 1               5                  10                  15

<210> SEQ ID NO 132
<211> LENGTH: 15
<212> TYPE: PRT
<213> ORGANISM: Homo sapiens
<220> FEATURE:
<223> OTHER INFORMATION: Rh50 GP Residues 311-325

<400> SEQUENCE: 132

Tyr Lys Phe Leu Thr Pro Leu Phe Thr Thr Lys Leu Arg Ile His
 1               5                  10                  15

<210> SEQ ID NO 133
<211> LENGTH: 15
<212> TYPE: PRT
<213> ORGANISM: Homo sapiens
<220> FEATURE:
<223> OTHER INFORMATION: Rh50 GP Residues 321-335

<400> SEQUENCE: 133

Lys Leu Arg Ile His Asp Thr Cys Gly Val His Asn Leu His Gly
 1               5                  10                  15

<210> SEQ ID NO 134
<211> LENGTH: 15
<212> TYPE: PRT
<213> ORGANISM: Homo sapiens
```

```
<220> FEATURE:
<223> OTHER INFORMATION: Rh50 GP Residues 331-345

<400> SEQUENCE: 134

His Asn Leu His Gly Leu Pro Gly Val Val Gly Gly Leu Ala Gly
  1               5                  10                  15

<210> SEQ ID NO 135
<211> LENGTH: 15
<212> TYPE: PRT
<213> ORGANISM: Homo sapiens
<220> FEATURE:
<223> OTHER INFORMATION: Rh50 GP Residues 341-355

<400> SEQUENCE: 135

Gly Gly Leu Ala Gly Ile Val Ala Val Ala Met Gly Ala Ser Asn
  1               5                  10                  15

<210> SEQ ID NO 136
<211> LENGTH: 15
<212> TYPE: PRT
<213> ORGANISM: Homo sapiens
<220> FEATURE:
<223> OTHER INFORMATION: Rh50 GP Residues 351-365

<400> SEQUENCE: 136

Met Gly Ala Ser Asn Thr Ser Met Ala Met Gln Ala Ala Ala Leu
  1               5                  10                  15

<210> SEQ ID NO 137
<211> LENGTH: 15
<212> TYPE: PRT
<213> ORGANISM: Homo sapiens
<220> FEATURE:
<223> OTHER INFORMATION: Rh50 GP Residues 361-375

<400> SEQUENCE: 137

Gln Ala Ala Ala Leu Gly Ser Ser Ile Gly Thr Ala Val Val Gly
  1               5                  10                  15

<210> SEQ ID NO 138
<211> LENGTH: 15
<212> TYPE: PRT
<213> ORGANISM: Homo sapiens
<220> FEATURE:
<223> OTHER INFORMATION: Rh50 GP Residues 371-385

<400> SEQUENCE: 138

Thr Ala Val Val Gly Gly Leu Met Thr Gly Leu Ile Leu Lys Leu
  1               5                  10                  15

<210> SEQ ID NO 139
<211> LENGTH: 15
<212> TYPE: PRT
<213> ORGANISM: Homo sapiens
<220> FEATURE:
<223> OTHER INFORMATION: Rh50 GP Residues 381-395

<400> SEQUENCE: 139

Leu Ile Leu Lys Leu Pro Leu Trp Gly Gln Pro Ser Asp Gln Asn
  1               5                  10                  15

<210> SEQ ID NO 140
<211> LENGTH: 15
<212> TYPE: PRT
<213> ORGANISM: Homo sapiens
<220> FEATURE:
```

```
<223> OTHER INFORMATION: Rh50 GP Residues 391-405

<400> SEQUENCE: 140

Pro Ser Asp Gln Asn Cys Tyr Asp Asp Ser Val Tyr Trp Lys Val
 1               5                  10                  15

<210> SEQ ID NO 141
<211> LENGTH: 15
<212> TYPE: PRT
<213> ORGANISM: Homo sapiens
<220> FEATURE:
<223> OTHER INFORMATION: Rh50 GP Residues 395-409

<400> SEQUENCE: 141

Asn Cys Tyr Asp Asp Ser Val Tyr Trp Lys Val Pro Lys Thr Arg
 1               5                  10                  15

<210> SEQ ID NO 142
<211> LENGTH: 16
<212> TYPE: PRT
<213> ORGANISM: Homo sapiens
<220> FEATURE:
<223> OTHER INFORMATION: BR

<400> SEQUENCE: 142

Ser Lys Tyr Pro Asn Cys Ala Tyr Lys Thr Thr Gln Ala Asn Lys His
 1               5                  10                  15

<210> SEQ ID NO 143
<211> LENGTH: 15
<212> TYPE: PRT
<213> ORGANISM: Homo sapiens
<220> FEATURE:
<223> OTHER INFORMATION: AV2

<400> SEQUENCE: 143

Thr Ile Pro Glu Gln Ser Phe Gln Gly Ser Pro Ser Ala Asp Thr
 1               5                  10                  15

<210> SEQ ID NO 144
<211> LENGTH: 15
<212> TYPE: PRT
<213> ORGANISM: Homo sapiens
<220> FEATURE:
<223> OTHER INFORMATION: AV4

<400> SEQUENCE: 144

Thr Val Lys Ala Asp Phe Glu Phe Ser Ser Ala Pro Ala Pro Asp
 1               5                  10                  15

<210> SEQ ID NO 145
<211> LENGTH: 15
<212> TYPE: PRT
<213> ORGANISM: Homo sapiens
<220> FEATURE:
<223> OTHER INFORMATION: AV6

<400> SEQUENCE: 145

Thr Val Glu Glu Arg Gln Gln Phe Gly Glu Leu Pro Val Ser Glu
 1               5                  10                  15

<210> SEQ ID NO 146
<211> LENGTH: 16
<212> TYPE: PRT
<213> ORGANISM: Homo sapiens
<220> FEATURE:
<223> OTHER INFORMATION: P23
```

```
<400> SEQUENCE: 146

Glu Leu Lys Ile Ile Ser Arg Cys Gln Val Cys Met Lys Lys Arg His
 1               5                  10                  15

<210> SEQ ID NO 147
<211> LENGTH: 13
<212> TYPE: PRT
<213> ORGANISM: Homo sapiens
<220> FEATURE:
<223> OTHER INFORMATION: HA

<400> SEQUENCE: 147

Pro Lys Tyr Val Lys Gln Asn Thr Leu Lys Leu Ala Thr
 1               5                  10

<210> SEQ ID NO 148
<211> LENGTH: 417
<212> TYPE: PRT
<213> ORGANISM: Homo sapiens
<220> FEATURE:
<223> OTHER INFORMATION: RhCE Residues 111-125

<400> SEQUENCE: 148

Met Ser Ser Lys Tyr Pro Arg Ser Val Arg Arg Cys Leu Pro Leu Cys
 1               5                  10                  15

Ala Leu Thr Leu Glu Ala Ala Leu Ile Leu Leu Phe Tyr Phe Phe Thr
                20                  25                  30

His Tyr Asp Ala Ser Leu Glu Asp Gln Lys Gly Leu Val Ala Ser Tyr
            35                  40                  45

Gln Val Gly Gln Asp Leu Thr Val Met Ala Ala Ile Gly Leu Gly Phe
        50                  55                  60

Leu Thr Ser Ser Phe Arg Arg His Ser Trp Ser Ser Val Ala Phe Asn
 65                  70                  75                  80

Leu Phe Met Leu Ala Leu Gly Val Gln Trp Ala Ile Leu Leu Asp Gly
                85                  90                  95

Phe Leu Ser Gln Phe Pro Ser Gly Lys Val Val Ile Thr Leu Phe Ser
            100                 105                 110

Ile Arg Leu Ala Thr Met Ser Ala Met Ser Val Leu Ile Ser Ala Gly
        115                 120                 125

Ala Val Leu Gly Lys Val Asn Leu Ala Gln Leu Val Met Val Leu
        130                 135                 140

Val Glu Val Thr Ala Leu Gly Thr Leu Arg Met Val Ile Ser Asn Ile
145                 150                 155                 160

Phe Asn Thr Asp Tyr His Met Asn Leu Arg His Phe Tyr Val Phe Ala
                165                 170                 175

Ala Tyr Phe Gly Leu Thr Val Ala Trp Cys Leu Pro Lys Pro Leu Pro
            180                 185                 190

Lys Gly Thr Glu Asp Asn Asp Gln Arg Ala Thr Ile Pro Ser Leu Ser
        195                 200                 205

Ala Met Leu Gly Ala Leu Phe Leu Trp Met Phe Trp Pro Ser Val Asn
    210                 215                 220

Ser Pro Leu Leu Arg Ser Pro Ile Gln Arg Lys Asn Ala Met Phe Asn
225                 230                 235                 240

Thr Tyr Tyr Ala Leu Ala Val Ser Val Thr Ala Ile Ser Gly Ser
                245                 250                 255

Ser Leu Ala His Pro Gln Arg Lys Ile Ser Met Thr Tyr Val His Ser
            260                 265                 270
```

```
Ala Val Leu Ala Gly Gly Val Ala Val Gly Thr Ser Cys His Leu Ile
            275                 280                 285
Pro Ser Pro Trp Leu Ala Met Val Leu Gly Leu Val Ala Gly Leu Ile
        290                 295                 300
Ser Ile Gly Gly Ala Lys Cys Leu Pro Val Cys Cys Asn Arg Val Leu
305                 310                 315                 320
Gly Ile His His Ile Ser Val Met His Ser Ile Phe Ser Leu Leu Gly
                325                 330                 335
Leu Leu Gly Glu Ile Thr Tyr Ile Val Leu Leu Val Leu His Thr Val
            340                 345                 350
Trp Asn Gly Asn Gly Met Ile Gly Phe Gln Val Leu Leu Ser Ile Gly
        355                 360                 365
Glu Leu Ser Leu Ala Ile Val Ile Ala Leu Thr Ser Gly Leu Leu Thr
    370                 375                 380
Gly Leu Leu Leu Asn Leu Lys Ile Trp Lys Ala Pro His Val Ala Lys
385                 390                 395                 400
Tyr Phe Asp Asp Gln Val Phe Trp Lys Phe Pro His Leu Ala Val Gly
                405                 410                 415
Phe

<210> SEQ ID NO 149
<211> LENGTH: 417
<212> TYPE: PRT
<213> ORGANISM: Homo sapiens
<220> FEATURE:
<223> OTHER INFORMATION: RhCe Residues 121-135

<400> SEQUENCE: 149

Met Ser Ser Lys Tyr Pro Arg Ser Val Arg Arg Cys Leu Pro Leu Cys
1               5                   10                  15
Ala Leu Thr Leu Glu Ala Ala Leu Ile Leu Leu Phe Tyr Phe Phe Thr
            20                  25                  30
His Tyr Asp Ala Ser Leu Glu Asp Gln Lys Gly Leu Val Ala Ser Tyr
        35                  40                  45
Gln Val Gly Gln Asp Leu Thr Val Met Ala Ala Ile Gly Leu Gly Phe
    50                  55                  60
Leu Thr Ser Ser Phe Arg Arg His Ser Trp Ser Ser Val Ala Phe Asn
65                  70                  75                  80
Leu Phe Met Leu Ala Leu Gly Val Gln Trp Ala Ile Leu Leu Asp Gly
                85                  90                  95
Phe Leu Ser Gln Phe Pro Ser Gly Lys Val Val Ile Thr Leu Phe Ser
            100                 105                 110
Ile Arg Leu Ala Thr Met Ser Ala Met Ser Val Leu Ile Ser Ala Gly
        115                 120                 125
Ala Val Leu Gly Lys Val Asn Leu Ala Gln Leu Val Val Met Val Leu
    130                 135                 140
Val Glu Val Thr Ala Leu Gly Thr Leu Arg Met Val Ile Ser Asn Ile
145                 150                 155                 160
Phe Asn Thr Asp Tyr His Met Asn Leu Arg His Phe Tyr Val Phe Ala
                165                 170                 175
Ala Tyr Phe Gly Leu Thr Val Ala Trp Cys Leu Pro Lys Pro Leu Pro
            180                 185                 190
Lys Gly Thr Glu Asp Asn Asp Gln Arg Ala Thr Ile Pro Ser Leu Ser
        195                 200                 205
```

```
Ala Met Leu Gly Ala Leu Phe Leu Trp Met Phe Trp Pro Ser Val Asn
210                 215                 220

Ser Ala Leu Leu Arg Ser Pro Ile Gln Arg Lys Asn Ala Met Phe Asn
225                 230                 235                 240

Thr Tyr Tyr Ala Leu Ala Val Ser Val Val Thr Ala Ile Ser Gly Ser
            245                 250                 255

Ser Leu Ala His Pro Gln Arg Lys Ile Ser Met Thr Tyr Val His Ser
            260                 265                 270

Ala Val Leu Ala Gly Gly Val Ala Val Gly Thr Ser Cys His Leu Ile
        275                 280                 285

Pro Ser Pro Trp Leu Ala Met Val Leu Gly Leu Val Ala Gly Leu Ile
        290                 295                 300

Ser Ile Gly Gly Ala Lys Cys Leu Pro Val Cys Cys Asn Arg Val Leu
305                 310                 315                 320

Gly Ile His His Ile Ser Val Met His Ser Ile Phe Ser Leu Leu Gly
                325                 330                 335

Leu Leu Gly Glu Ile Thr Tyr Ile Val Leu Leu Val Leu His Thr Val
            340                 345                 350

Trp Asn Gly Asn Gly Met Ile Gly Phe Gln Val Leu Leu Ser Ile Gly
            355                 360                 365

Glu Leu Ser Leu Ala Ile Val Ile Ala Leu Thr Ser Gly Leu Leu Thr
370                 375                 380

Gly Leu Leu Asn Leu Lys Ile Trp Lys Ala Pro His Val Ala Lys
385                 390                 395                 400

Tyr Phe Asp Asp Gln Val Phe Trp Lys Phe Pro His Leu Ala Val Gly
                405                 410                 415

Phe

<210> SEQ ID NO 150
<211> LENGTH: 417
<212> TYPE: PRT
<213> ORGANISM: Homo sapiens
<220> FEATURE:
<223> OTHER INFORMATION: RhcE Residues 131-145

<400> SEQUENCE: 150

Met Ser Ser Lys Tyr Pro Arg Ser Val Arg Arg Cys Leu Pro Leu Trp
1               5                   10                  15

Ala Leu Thr Leu Glu Ala Ala Leu Ile Leu Leu Phe Tyr Phe Phe Thr
                20                  25                  30

His Tyr Asp Ala Ser Leu Glu Asp Gln Lys Gly Leu Val Ala Ser Tyr
            35                  40                  45

Gln Val Gly Gln Asp Leu Thr Val Met Ala Ala Leu Gly Leu Gly Phe
        50                  55                  60

Leu Thr Ser Asn Phe Arg Arg His Ser Trp Ser Ser Val Ala Phe Asn
65                  70                  75                  80

Leu Phe Met Leu Ala Leu Gly Val Gln Trp Ala Ile Leu Leu Asp Gly
                85                  90                  95

Phe Leu Ser Gln Phe Pro Pro Gly Lys Val Val Ile Thr Leu Phe Ser
                100                 105                 110

Ile Arg Leu Ala Thr Met Ser Ala Met Ser Val Leu Ile Ser Ala Gly
            115                 120                 125

Ala Val Leu Gly Lys Val Asn Leu Ala Gln Leu Val Met Val Leu
        130                 135                 140

Val Glu Val Thr Ala Leu Gly Thr Leu Arg Met Val Ile Ser Asn Ile
```

-continued

```
                145                 150                 155                 160
Phe Asn Thr Asp Tyr His Met Asn Leu Arg His Phe Tyr Val Phe Ala
                    165                 170                 175
Ala Tyr Phe Gly Leu Thr Val Ala Trp Cys Leu Pro Lys Pro Leu Pro
            180                 185                 190
Lys Gly Thr Glu Asp Asn Asp Gln Arg Ala Thr Ile Pro Ser Leu Ser
                195                 200                 205
Ala Met Leu Gly Ala Leu Phe Leu Trp Met Phe Trp Pro Ser Val Asn
        210                 215                 220
Ser Pro Leu Leu Arg Ser Pro Ile Gln Arg Lys Asn Ala Met Phe Asn
225                 230                 235                 240
Thr Tyr Tyr Ala Leu Ala Val Ser Val Val Thr Ala Ile Ser Gly Ser
                245                 250                 255
Ser Leu Ala His Pro Gln Arg Lys Ile Ser Met Thr Tyr Val His Ser
                260                 265                 270
Ala Val Leu Ala Gly Gly Val Ala Val Gly Thr Ser Cys His Leu Ile
            275                 280                 285
Pro Ser Pro Trp Leu Ala Met Val Leu Gly Leu Val Ala Gly Leu Ile
        290                 295                 300
Ser Ile Gly Gly Ala Lys Cys Leu Pro Val Cys Cys Asn Arg Val Leu
305                 310                 315                 320
Gly Ile His His Ile Ser Val Met His Ser Ile Phe Ser Leu Leu Gly
                325                 330                 335
Leu Leu Gly Glu Ile Thr Tyr Ile Val Leu Leu Val Leu His Thr Val
                340                 345                 350
Trp Asn Gly Asn Gly Met Ile Gly Phe Gln Val Leu Leu Ser Ile Gly
            355                 360                 365
Glu Leu Ser Leu Ala Ile Val Ile Ala Leu Thr Ser Gly Leu Leu Thr
        370                 375                 380
Gly Leu Leu Leu Asn Leu Lys Ile Trp Lys Ala Pro His Val Ala Lys
385                 390                 395                 400
Tyr Phe Asp Asp Gln Val Phe Trp Lys Phe Pro His Leu Ala Val Gly
                405                 410                 415
Phe

<210> SEQ ID NO 151
<211> LENGTH: 417
<212> TYPE: PRT
<213> ORGANISM: Homo sapiens
<220> FEATURE:
<223> OTHER INFORMATION: RhD Residues 141-155

<400> SEQUENCE: 151

Met Ser Ser Lys Tyr Pro Arg Ser Val Arg Arg Cys Leu Pro Leu Trp
1               5                   10                  15
Ala Leu Thr Leu Glu Ala Ala Leu Ile Leu Leu Phe Tyr Phe Phe Thr
                20                  25                  30
His Tyr Asp Ala Ser Leu Glu Asp Gln Lys Gly Leu Val Ala Ser Tyr
            35                  40                  45
Gln Val Gly Gln Asp Leu Thr Val Met Ala Ala Ile Gly Leu Gly Phe
        50                  55                  60
Leu Thr Ser Ser Phe Arg Arg His Ser Trp Ser Ser Val Ala Phe Asn
65                  70                  75                  80
Leu Phe Met Leu Ala Leu Gly Val Gln Trp Ala Ile Leu Leu Asp Gly
                85                  90                  95
```

```
Phe Leu Ser Gln Phe Pro Ser Gly Lys Val Ile Thr Leu Phe Ser
                100                 105                 110

Ile Arg Leu Ala Thr Met Ser Ala Leu Ser Val Leu Ile Ser Val Asp
        115                 120                 125

Ala Val Leu Gly Lys Val Asn Leu Ala Gln Leu Val Met Val Leu
        130                 135                 140

Val Glu Val Thr Ala Leu Gly Asn Leu Arg Met Val Ile Ser Asn Ile
145                 150                 155                 160

Phe Asn Thr Asp Tyr His Met Asn Met Met His Ile Tyr Val Phe Ala
                165                 170                 175

Ala Tyr Phe Gly Leu Ser Val Ala Trp Cys Leu Pro Lys Pro Leu Pro
        180                 185                 190

Glu Gly Thr Glu Asp Asn Asp Gln Thr Ala Thr Ile Pro Ser Leu Ser
        195                 200                 205

Ala Met Leu Gly Ala Leu Phe Leu Trp Ile Phe Trp Pro Ser Phe Asn
        210                 215                 220

Ser Ala Leu Leu Arg Ser Pro Ile Glu Arg Lys Asn Ala Val Phe Asn
225                 230                 235                 240

Thr Tyr Tyr Ala Val Ala Val Ser Val Val Thr Ala Ile Ser Gly Ser
                245                 250                 255

Ser Leu Ala His Pro Gln Gly Lys Ile Ser Lys Thr Tyr Val His Ser
        260                 265                 270

Ala Val Leu Ala Gly Gly Val Ala Val Gly Thr Ser Cys His Leu Ile
        275                 280                 285

Pro Ser Pro Trp Leu Ala Met Val Leu Gly Leu Val Ala Gly Leu Ile
        290                 295                 300

Ser Val Gly Gly Ala Lys Tyr Leu Pro Gly Cys Cys Asn Arg Val Leu
305                 310                 315                 320

Gly Ile Pro His Ser Ser Ile Met Gly Tyr Asn Phe Ser Leu Leu Gly
                325                 330                 335

Leu Leu Gly Glu Ile Ile Tyr Ile Val Leu Leu Val Leu Asp Thr Val
        340                 345                 350

Gly Ala Gly Asn Gly Met Ile Gly Phe Gln Val Leu Leu Ser Ile Gly
        355                 360                 365

Glu Leu Ser Leu Ala Ile Val Ile Ala Leu Thr Ser Gly Leu Leu Thr
370                 375                 380

Gly Leu Leu Asn Leu Lys Ile Trp Lys Ala Pro His Glu Ala Lys
385                 390                 395                 400

Tyr Phe Asp Asp Gln Val Phe Trp Lys Phe Pro His Leu Ala Val Gly
                405                 410                 415

Phe

<210> SEQ ID NO 152
<211> LENGTH: 417
<212> TYPE: PRT
<213> ORGANISM: Homo sapiens
<220> FEATURE:
<223> OTHER INFORMATION: RhCe Residues 151-165

<400> SEQUENCE: 152

Met Ser Ser Lys Tyr Pro Arg Ser Val Arg Arg Cys Leu Pro Leu Trp
 1               5                  10                  15

Ala Leu Thr Leu Glu Ala Ala Leu Ile Leu Leu Phe Tyr Phe Phe Thr
                20                  25                  30
```

```
His Tyr Asp Ala Ser Leu Glu Asp Gln Lys Gly Leu Val Ala Ser Tyr
             35                  40                  45

Gln Val Gly Gln Asp Leu Thr Val Met Ala Ala Leu Gly Leu Gly Phe
 50                  55                  60

Leu Thr Ser Asn Phe Arg Arg His Ser Trp Ser Val Ala Phe Asn
 65                  70                  75                  80

Leu Phe Met Leu Ala Leu Gly Val Gln Trp Ala Ile Leu Leu Asp Gly
                 85                  90                  95

Phe Leu Ser Gln Phe Pro Pro Gly Lys Val Val Ile Thr Leu Phe Ser
                100                 105                 110

Ile Arg Leu Ala Thr Met Ser Ala Met Ser Val Leu Ile Ser Ala Gly
             115                 120                 125

Ala Val Leu Gly Lys Val Asn Leu Ala Gln Leu Val Met Val Leu
            130                 135                 140

Val Glu Val Thr Ala Leu Gly Thr Leu Arg Met Val Ile Ser Asn Ile
145                 150                 155                 160

Phe Asn Thr Asp Tyr His Met Asn Leu Arg His Phe Tyr Val Phe Ala
                165                 170                 175

Ala Tyr Phe Gly Leu Thr Val Ala Trp Cys Leu Pro Lys Pro Leu Pro
                180                 185                 190

Lys Gly Thr Glu Asp Asn Asp Gln Arg Ala Thr Ile Pro Ser Leu Ser
            195                 200                 205

Ala Met Leu Gly Ala Leu Phe Leu Trp Met Phe Trp Pro Ser Val Asn
            210                 215                 220

Ser Ala Leu Leu Arg Ser Pro Ile Gln Arg Lys Asn Ala Met Phe Asn
225                 230                 235                 240

Thr Tyr Tyr Ala Leu Ala Val Ser Val Val Thr Ala Ile Ser Gly Ser
                245                 250                 255

Ser Leu Ala His Pro Gln Arg Lys Ile Ser Met Thr Tyr Val His Ser
            260                 265                 270

Ala Val Leu Ala Gly Gly Val Ala Val Gly Thr Ser Cys His Leu Ile
            275                 280                 285

Pro Ser Pro Trp Leu Ala Met Val Leu Gly Leu Val Ala Gly Leu Ile
290                 295                 300

Ser Ile Gly Gly Ala Lys Cys Leu Pro Val Cys Cys Asn Arg Val Leu
305                 310                 315                 320

Gly Ile His His Ile Ser Val Met His Ser Ile Phe Ser Leu Leu Gly
                325                 330                 335

Leu Leu Gly Glu Ile Thr Tyr Ile Val Leu Leu Val Leu His Thr Val
            340                 345                 350

Trp Asn Gly Asn Gly Met Ile Gly Phe Gln Val Leu Leu Ser Ile Gly
            355                 360                 365

Glu Leu Ser Leu Ala Ile Val Ile Ala Leu Thr Ser Gly Leu Leu Thr
370                 375                 380

Gly Leu Leu Leu Asn Leu Lys Ile Trp Lys Ala Pro His Val Ala Lys
385                 390                 395                 400

Tyr Phe Asp Asp Gln Val Phe Trp Lys Phe Pro His Leu Ala Val Gly
                405                 410                 415

Phe
```

ALLO AND AUTO-REACTIVE T-CELL EPITOPES

The present invention relates to the mapping of allo-reactive T-cell epitopes on the rhesus (RhD and RhCc/Ee) proteins and to the use of such epitopes to modulate the corresponding immune responses to these antigens.

Human blood contains a genetically complex rhesus (Rh) blood group system. For example, humans are either RhD positive or negative and this can lead to problems during transfusions or pregnancy when RhD negative individuals are exposed to RhD positive blood and become immunised to produce anti-D.

The most important allele in the RhD blood group system is the D antigen. The RhD antigen is carried by the RhD protein which is a transmembrane protein consisting of 417 amino acids with 12 putative transmembrane domains and 6 extracellular loops. A series of peptides have been constructed in the present invention based on the RhD protein each being 15 amino acids (AA) long, and tested in vitro against T-lymphocytes from normal individuals, donors who have been alloimmunised to produce anti-D, and patients with warm type autoimmune haemolytic anaemia.

The full amino acid sequence of the RhCE polypeptide and the differences in sequence for c, e and D polypeptides is shown in FIG. 1 hereinafter (Reference: The Blood Group Antigen Facts Book, p94, Editors; M E Reid & C Lomas-Francis, Academic Press London).

The complexity of the blood system can cause problems during pregnancy when a woman who is RhD negative is carrying a RhD positive foetus, as the woman is at risk of being immunized by the RhD positive blood cells of her own baby. This immunisation can take place during situations when the other's and baby's blood can become mixed, for example during amniocentesis, antepartum haemorrhage but mainly at parturition.

Once the mother's immune system has been exposed to RhD positive blood cells, she will produce anti-D antibodies which can cross the placenta and cause Rh haemolytic disease in any subsequent RhD positive pregnancies. Such haemolytic disease can be fatal for the neonate.

Currently, purified anti-D immunoglobulin is injected whenever a mother is exposed to fetal RhD positive red blood cells which may occur during e.g., amniocentesis, antepartum haemorrhage but mainly at parturition. About 17% of Caucasian women are RhD negative so that most industrialized countries have RhD prevention programmes wherein all RhD negative women receive prophylaxis with anti-D immunoglobulin at delivery or in association with the other high risk events alluded to above. Further in many countries, routine antepartum prophylaxis to minimize the incidence of Rh haemolytic disease is practised.

There are a number of problems with this approach. In the first place efficacy is never entirely complete since events can be missed or undeclared or a foetal haemorrhage can be larger than the anti-D can neutralize. Secondly, current anti-D immunoglobulin comes from deliberately immunised donors, which puts volunteers, often male (paid or not) at some small risk. In addition it takes at least 12 months to accredit the donors during which time their blood products are not available. For these reasons there is a worldwide shortage of anti-D immunoglobulin. Finally, there are also concerns about the safety of recipients who may be exposed to transfusion transmitted infections such as by inadvertent infection with agents, for example variant Creutzfeld-Jacob Disease (vCJD) for which there is no satisfactory test.

Other groups that can be at risk from alloimmunisation are those who are regular recipients of bloods products, for example those suffering from haemological malignant disease, sickle cell disease or thalassaemia.

Certain RhD peptides have been found to specifically stimulate the helper T-cells of alloimmunised individuals. Conversely, certain RhD peptides have been found to stimulate the production of immunosuppressive cytokines by helper T-cells. There is furthermore some correlation between the HLA-DR type of allo- and auto-immunised donors and the peptides which stimulate helper T-cell responses.

An object of the present invention is to provide an effective treatment for subjects that have become alloimmunised or have an autoimmune disease against red blood cells.

A further objective of the invention is to provide an effective prophylactic to prevent alloimmunisation.

In a first embodiment of the invention there is provided a pharmaceutical composition for the prevention of alloimmunisation of a subject, said composition comprising an immunologically effective epitope of a rhesus protein or an immunologically active analogue or derivative thereof.

We have mapped helper T-cell epitopes on the RhD protein. The characterization of a helper epitope that is targeted in most alloimmunised donors and the identification of correlations between HLA-DR type and particular dominant epitopes opens the way for the evaluation of peptide immunotherapy as a novel way to regulate the immune response to RhD and to prevent Rh haemolytic disease and anti-D related transfusion problems.

Currently, anti-D which is given to pregnant women during significant events in pregnancy may be considered as a passive form of immunotherapy because it has the effect of blocking the effects of immune events on a temporary basis.

The replacement of passive with active peptide immunotherapy in RhD negative women is an attractive option since safe synthetic tolerogens can be developed and given before pregnancy thus avoiding foetal exposure. Suppression throughout pregnancy would mean that only one injection was necessary, considerably simplifying management of RhD negative women and also it may be possible for the first time to reverse rather than prevent alloimmunisation by administration of tolerogenic peptides to individuals who already have produced anti-D with the objective of "switching-off" the immune response to RhD.

Tolerogenic peptides to other Rh antigens, as determined by the current invention, would be of equivalent value in preventing, or modifying the production of alloantibodies by the respective antigens, including (but not exclusively) RhC, Rhc, RhE and Rhe; and Rh50 (peptides are shown in Table 4) in autoimmune haemolytic anaemia.

Accordingly the categories of individual in whom prior immunization would be considered are as follows:—

(1) All women during their child bearing years; and (2) regular recipients of blood products; who might be exposed to blood transfusion for example haemological malignant disease, sickle cell disease and thalassaemia.

Such a pharmaceutical composition can be given to expectant mothers with RhD negative blood and a RhD positive child in this respect, the composition would result in the mother not producing an immune response at any occasion when the foetuses blood comes in contact with her own immune system. In this connection, there is a reduced likelihood that any subsequent baby which is RhD positive would suffer from haemolytic disease.

The use of synthetic peptides in accordance with the present invention removes concerns about viral infection being transmitted either by anti-D immunoglobulin used for passive immunotherapy or by red blood cells given to volunteer recipients. The time consuming and expensive procedures required to validate accredited donors and donations are also important considerations.

In addition, by use of these compositions, volunteers who are often RhD negative men, can avoid the usual injection of red blood cells when they are deliberately immunised for the production of anti-D immunoglobulin.

In a second embodiment of the invention there is provided a pharmaceutical composition for the immunosuppression of a response elicited by alloimmunisation of a subject or an autoimmune haemolytic disease, said composition comprising an immunologically effective epitope of a rhesus protein or an immunologically active analogue or derivative thereof.

If the immune system of an RhD negative mother has already been in contact with the blood from a RhD positive baby, such a composition can used during subsequent pregnancies with a RhD positive baby to reduce the likelihood of the baby suffering from RhD haemolytic disease.

In addition, such a composition can be given to patients who have accidentally been given an RhD positive blood transfusion when they are RhD negative. In this connection, the availability of such a composition reduces the need for very large doses of anti-D immunoglobulin for prophylaxis and the likelihood of becoming alloimmunised thereafter.

Preferably autoimmune disease is idiopathic or secondary autoimmune haemolytic anaemia mediated by 'warm-type' autoantibodies. The trigger for this autoimmune disease is unknown and therefore it may occur at anytime and results in the body producing autoantibodies of broad Rh group specificity which attack the bodies own red blood cells.

Conveniently the rhesus protein is either RhD, RhC, Rhc, RhE or Rhe protein.

These determine the main Rh-specific antigens found on the surface of a red blood cell.

In a preferred embodiment an epitope selected from at least one of numbers 2, 5, 6, 6A, 10A, 11, 11A, 12, 12A, 14, 15A, 18A, 28, 29, 31, 38 and 39 hereinbefore set forth.

The aforementioned are the most common epitopes recognised by T-cells of alloimmunised subjects and those suffering from autoimmune haemolytic anaemia. In autoimmune haemolytic anaemia, the preferred epitopes are 2, 5, 14, 29, 31 and 38. Therefore induced tolerance to such epitopes would stop an immune response being mounted if they appear in the blood of the subject.

Preferably the epitope is either epitope 12A or 29 since epitope 12A is the most common epitope recognised by alloreactive T-cells, epitope 29 is most commonly recognised in autoimmune haemolytic anaemia.

Conveniently any of the epitopes or immunoreactive derivatives can be synthesised.

If the epitope sequences are artificially synthesised microbial contamination is negligible. In a third embodiment of the invention there is provided a pharmaceutical composition for the induction of alloimmunisation of a subject, said composition comprising an immunologically effective epitope of a rhesus protein or an immunologically active analogue or derivative thereof disposed in a pharmacologically acceptable vehicle.

Preferably the rhesus protein is either RhD, RhC, Rhc, RhE or Rhe protein, conveniently an epitope selected from at least one of numbers 2, 5, 6, 6A, 10A, 11, 11A, 12, 12A, 14, 15A, 18A, 28, 29, 31, 38 and 39 hereinbefore set forth.

Preferably the vehicle is selected such that the composition is in an injectable, oral, rectal, topical or spray-uptake form.

It is known that mammals may be tolerised to certain stimuli by taking in specific peptide fragments, for example from the nasal mucosa or via the gut. We propose that a good way of abolishing the immune response to RhD in recipient females prior to, during, or after pregnancy is to administer rhesus peptides via the mucosa such as the nasal, buccal, or anal mucosa or transdermally. The peptide fragments in accordance with the present invention will enter via mucosal tissues and effectively tolerise the subject without causing a full blown immune response which may well be the case should the peptide fragments of the present invention reach circulating blood system at the first instance.

In an injectable form the epitopes can be used to deliberately immunise the subject with an epitope which can for example produce IL-10 or TGF-β which have immunosuppressive effects.

The outcome of this approach is to develop a "vaccine" using Rh epitopes which will suppress the immune response to Rh proteins.

In a fourth embodiment of the invention there is provided a tolerising peptide fragment disposed in a pharmacologically effective vehicle, said vehicle being adapted for injection, oral, rectal via a suppository, topical or spray-uptake administration to the subject wherein the tolerising peptide fragment is selected from an epitope of either a RhD, RhC, Rhc, RhE or Rhe protein. Preferably the epitope is selected from at least one of epitope numbers 2, 5, 6, 6A, 10A, 11, 11A, 12, 12A, 14, 15A, 18A, 28, 29, 31, 38 and 39 hereinbefore set forth.

Thus the pharmaceutically acceptable vehicle may be adapted for transdermal or transmucosal administration or wherein said vehicle may be a formulation with an enteric coating for oral administration.

In a fifth embodiment of the present invention there is provided a method of tolerizing a subject which comprises administering to said subject a tolerising peptide fragment.

In a sixth embodiment of the present invention there is provided an epitope from a RhD, RhC, Rhc, RhE or Rhe protein selected from at least one of epitope numbers 2, 5, 6, 6A, 10A, 11, 11A, 12, 12A, 14, 15A, 18A, 28, 29, 31, 38 and 39.

In a seventh embodiment of the present invention there is provided the use in the manufacture of a medicament for the tolerisation of a patient who may become alloimmunised comprising an epitope selected from a RhD, RhC, Rhc, RhE or Rhe protein or selected from at least one of epitope numbers 2, 5, 6, 6A, 10A, 11, 11A, 12, 12A, 14, 15A, 18A, 28, 29, 31, 38 and 39 disposed in a pharmaceutically acceptable vehicle therefor.

In an eighth embodiment of the invention there is provided the use in the manufacture of a medicament for the immunosuppression of an alloimmunised patient or a patient with warm-type autoimmune haemolytic anaemia comprising an epitope selected from a RhD, RhC, Rhc, RhE or Rhe protein or selected from at least one of epitope numbers 2, 5, 6, 6A, 10A, 11, 11A, 12, 12A, 14, 15A, 18A, 28, 29, 31, 38 and 39 disposed in a pharmaceutically acceptable vehicle therefor.

In a ninth embodiment of the invention there is provided a method for determining the effect of an epitope from a rhesus protein on a human lymphocyte, in vitro, comprising the steps of:— a) stimulating the lymphocyte with one or more epitope of a rhesus protein;

b) between 4 and 7 days later resuspending the cultures and transferring aliquots into plates prepared in the following manner;

c) washing the plate at least once with Hanks Buffered Salt Solution (HBSS);

d) coating each well in the plate with monoclonal anti-cytokine capture antibody;

e) blocking any non-specific binding using an appropriate solution;

f) incubating the plates with the lymphocyte culture for 12-36 hours at 30-40° C. in an atmosphere of substantially 5% $CO_2$ and substantially 95% air;

g) washing the plates at least once with Tween/PBS;

h) introducing an appropriate biotinylated monoclonal detection antibody to each well and incubating for 30-60 min at room temperature;

I) washing the plates at least once with Tween/PBS;

j) introducing ExtrAvidin-alkaline phosphatase conjugate and incubating for 15-45 mins;

k) washing the plates again at least once with Tween/PBS;

l) developing the plates with p-nitrophenyl phosphate in 0.05M carbonate alkaline buffer pH9.6 added to each well; and m) reading the absorbance at 405 nm.

Traditionally, among other techniques, researchers have used a captive assay called ELISPOT to determine the amount of cytokines produced by a cell. This assay produces a colour spot for each cytokine producing cell. A crude calculation based on the number of coloured spots is then used to estimate the amount of cytokines produced. The use of p-nitrophenyl phosphate in the present assay allows the amount of cytokine captured by the antibody in the wall to be established on the basis of the colour change produced which can be measured by the more accurate method of spectrophotometry.

Accordingly, this method is very sensitive and therefore can identify that a particular RhD protein is capable of stimulating human T-cells to produce potentially immunosuppressive cytokines rather than to proliferate. This is important for the determination of the method of delivery of an epitope. An epitope which leads to T-cell proliferation may be given as a tolerogen through the nasal or mucosal route whereas an epitope which leads to immunosuppressive cytokines may be injected.

In a tenth embodiment of the present invention there is provided a method for the determination of the propensity of a RhD negative subject to produce anti-D antibodies after exposure to RhD positive blood comprising ascertaining the tissue type of the subject and determining if they are HLA-DRB1*15.

If the subject has a tissue type of HLA-DRB1*15 they are more likely to raise anti-D antibodies therefore they should be given treatment before being put at risk of exposure to RhD positive red blood cells.

The invention will now be described, by way of illustration only, with reference to the following examples and the accompanying figures.

FIG. 1 shows the full amino acid sequence of RhCE polypeptide; differences in the sequence for Rhc, Rhe and RhD polypeptides are also shown (Reference: The Blood Group Antigen Facts Book P94, Editor; M E Reid & C Lomas-Francis, Academic Press London).

FIG. 3A shows the distribution of stimulating RhD peptides in autoimmune haemolytic anaemia patients; x—RhD peptide stimulus; y—percentage of subjects responding to specific RhD peptides.

FIG. 3B shows the distribution of stimulating RhD peptides in normal controls; x—RhD peptide stimulus; y—percentage of subjects responding to specific RhD peptides.

Figure 4:
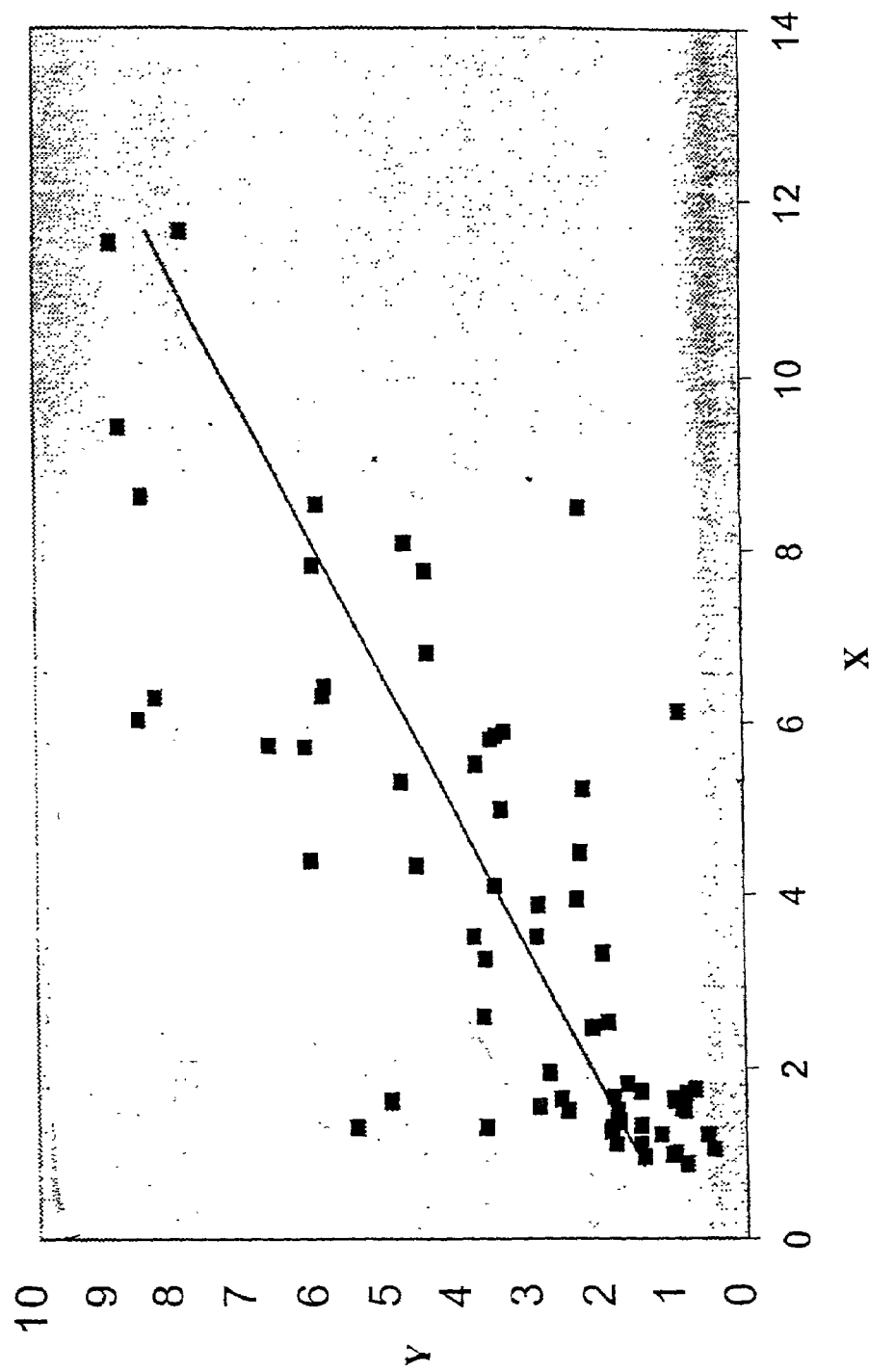

FIG. 4 shows the correlation between Rh epitopes recognised in donors sharing a tissue type. X and Y axes represent the stimulation indices for donors 1 and 2 respectively. Each square represents the response to a peptide. Correlation co-efficient (R)=0.774, p value 9.57E-015

Figure 5:
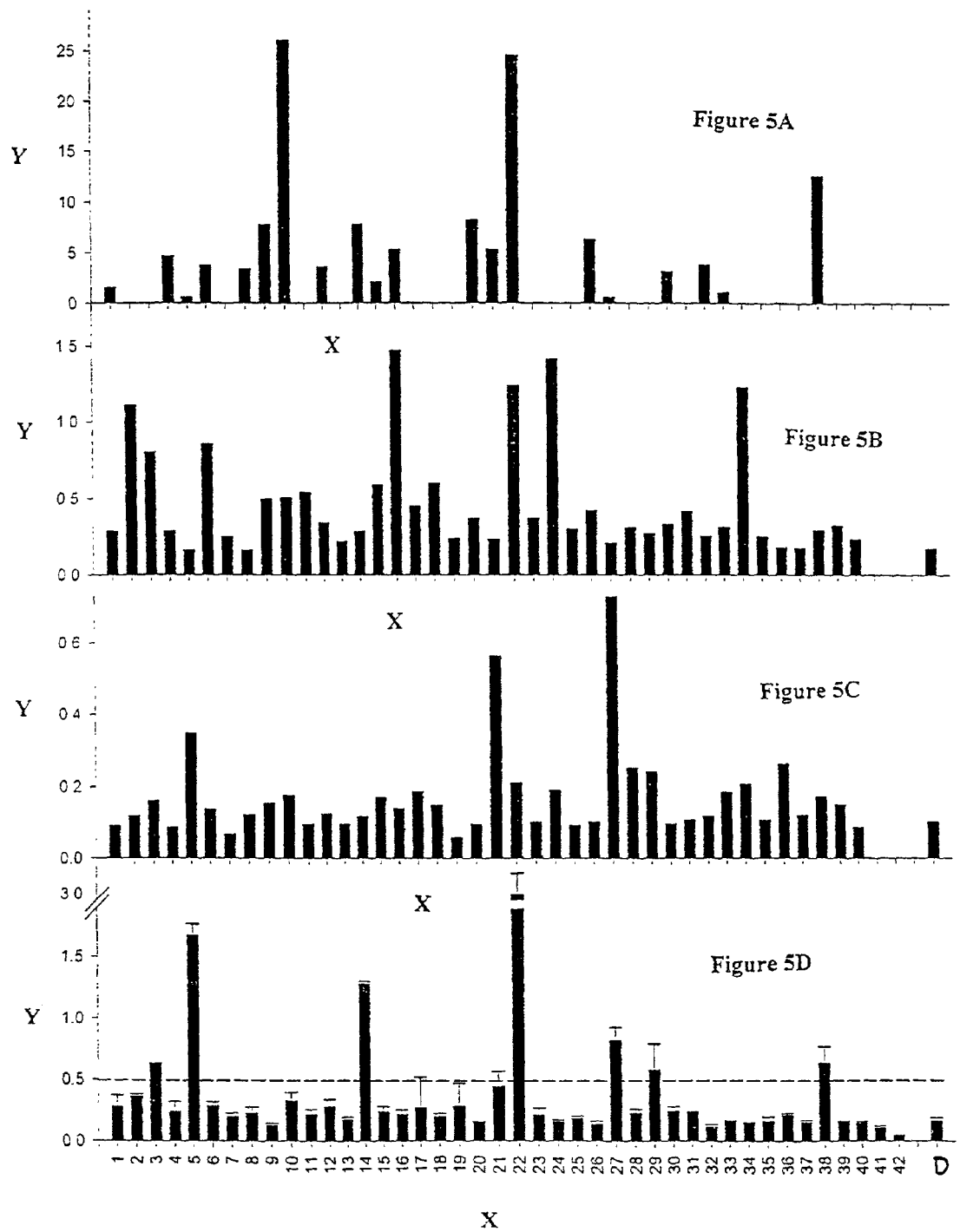

FIG. 5A shows the response pattern to the induction of TGF-β production of T-cells after incubation with Rh peptides; x—RhD peptide stimulus; y—TGF-β1 secretion (pg/ml). Value D=none.

FIG. 5B shows the response pattern to the induction of IL-10 production of T-cells after incubation with Rh peptides; x—RhD peptide stimulus; y—IL-10 secretion (ng/ml). Value D=none.

FIG. 5C shows the response pattern to the induction of IFN-γ production of T-cells after incubation with Rh peptides; x—RhD peptide stimulus; y—IFN-γ secretion (ng/ml). Value D=none.

FIG. 5D shows the amount of incorporation of $^3$H-Thymidine into T-cells after incubation with Rh peptides; x—RhD peptide stimulus; y—$^3$H-Thymidine incorporation (mean CPMx$10^{-3}$±SD) SI=3. Value D=none.

Figure 6:
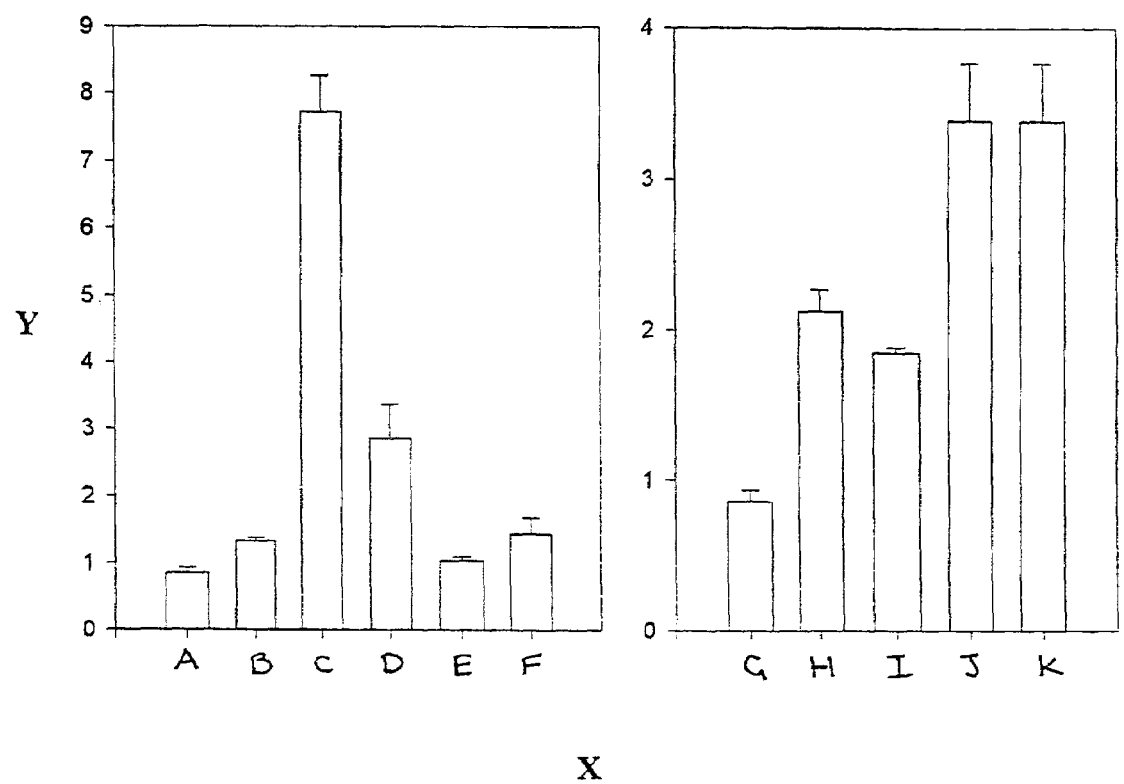

FIG. 6 shows the inhibition of T-cells that respond to RhD protein by peptides that generate an immunosuppressive cytokine response; x—RhD peptide stimulus; y—$^3$H-Thymidine incorporation (mean CPMx$10^{-3}$±SD). A—none; B—control (−); C—RhD; D—RhD & 16; E—RhD & 22; F—RhD & 24; G—none; H—PPD; I—PPD & 16; J—PPD & 22; K—PPD & 24.

EXAMPLE 1

Two complete panels of 68 15-mer peptides, with 5 or 10 amino acid overlaps, were synthesized (Multiple Peptide Service, Cambridge Research Biochemicals, Cheshire, UK and Dept. Of Biochemistry, University of Bristol, UK), corresponding to the sequences of the 30 kD Rh proteins associated with expression of the RhD or RhCc/Ee blood group antigens respectively. The amino acid sequences for each of these proteins were deduced independently from cDNA analyses by 2 laboratories. Since the two polypeptide sequences show 92% homology, 16 of the synthetic peptides were shared between the panels (numbering from the amino terminus, peptides 1-5, 8, 9, 14, 21, 28, 29, 37-39, 41 and 42). In order to ensure purity, each panel was synthesized by fluorenylmethoxycarbonyl chemistry on resin using a base-labile linker, rather than by conventional pin technology, and randomly selected peptides were screened for purity by HPLC and amino acid analysis. The peptides were used to stimulate cultures at 20 μg/ml, although it should be noted that the responses of the cultures had previously been shown to be similar in magnitude and kinetics at peptide concentration between 5-20 μg/ml.

The control antigens *Mycobacterium tuberculosis* purified protein derivative (PPD) (Statens Seruminstut, Denmark) and keyhole limpet hemocyanin (KLH) (Calbiochem-Behring, La Jolla, Calif., USA) were dialysed extensively against phosphate buffered saline pH 7.4 (PBS) and filter sterilized before addition to cultures at 50 µg/ml, PPD, but not KLH, readily provokes recall T-cell responses in vitro, since most UK citizens have been immunised with BCG. Concanavalin A (Con A) was obtained from Sigma, Poole, Dorset, UK, and used to stimulate cultures at 10 µg/ml.

Antibodies

FITC- or phycoerythrin-conjugated mAbs against human CD3, CD19, CD45 or CD14 were obtained from Dako UK Ltd. Blocking mAbs specific for HLA-DP, -DQ, or -DR supplied by Becton Dickinson (Oxford, UK) were dialysed thoroughly against PBS before addition to cultures at the previously determined optimum concentration of 2.5 µg/ml.

Isolation of Peripheral Blood Mononuclear Cells and T-Cells

Peripheral blood mononuclear cells (PBMC) from donors or patients were separated from fresh blood samples using Ficoll-Hypaque. The donors and patients had become alloimmunised with RhD positive blood either through pregnancy, a blood transfusion or through immunization with the relevant blood.

The viability of PBMC was greater than 90% in all experiments, as judged by trypan blue exclusion. T-cells were isolated from PBMC by passage through glass bead affinity columns coated with human IgG/sheep anti-human IgG immune complexes. Flow cytometry (Becton Dickinson FACScan) demonstrated that typical preparations contained more than 95% T-cells.

Cell Proliferation Assays

PBMC were cultured in 10041 volumes in microtitre plates at a concentration of $1.25 \times 10^6$ cells/ml in an Alpha Modification of Eagle's Medium (ICN Flow, Bucks UK) supplemented with 5% autologous serum, 4 mM L-Glutamine (Gibco, Paisley, UK), 100 U/ml sodium benzylpenicillin G (Sigma), 100 µg/ml streptomycin sulphate (Sigma), $5 \times 10^{-5}$M 2-mercaptoethanol (Sigma) and 20 mM HEPES pH7,2 (Sigma). All plates were incubated at 37° C. in a humidified atmosphere of 5% $CO_2$/95% air. The cell proliferation in cultures was estimated from the incorporation of $^3$H-Thymidine in triplicate wells 5 days after stimulation with antigen as described previously. Proliferation results are presented either as the mean CPM+/−SD of the triplicate samples, or as a stimulation index (SI), expressing the ratio of mean CPM in stimulated versus unstimulated control cultures. An S1>3 with CPM>1000 is interpreted as representing a positive response.

Activation Assay

The aforementioned experiments were designed to minimise the response by quiescent or naive T-cells that can recognise RhD protein, but which are not activated by immunisation. To validate the experiments, the T-cells proliferated in the aforementioned experiment were tested using a modification of the method set out in European Journal of Immunology (1994) 24: 1578-1582 to identify if they had been activated in Vivo. In this connection, the T-cells were screened to ascertain if they were from the subset bearing CD45RO which is a marker of previous activation or "memory", rather than from the subset bearing CD45RA which is the marker of quiescent or "naive" T-cells.

Figure 2:
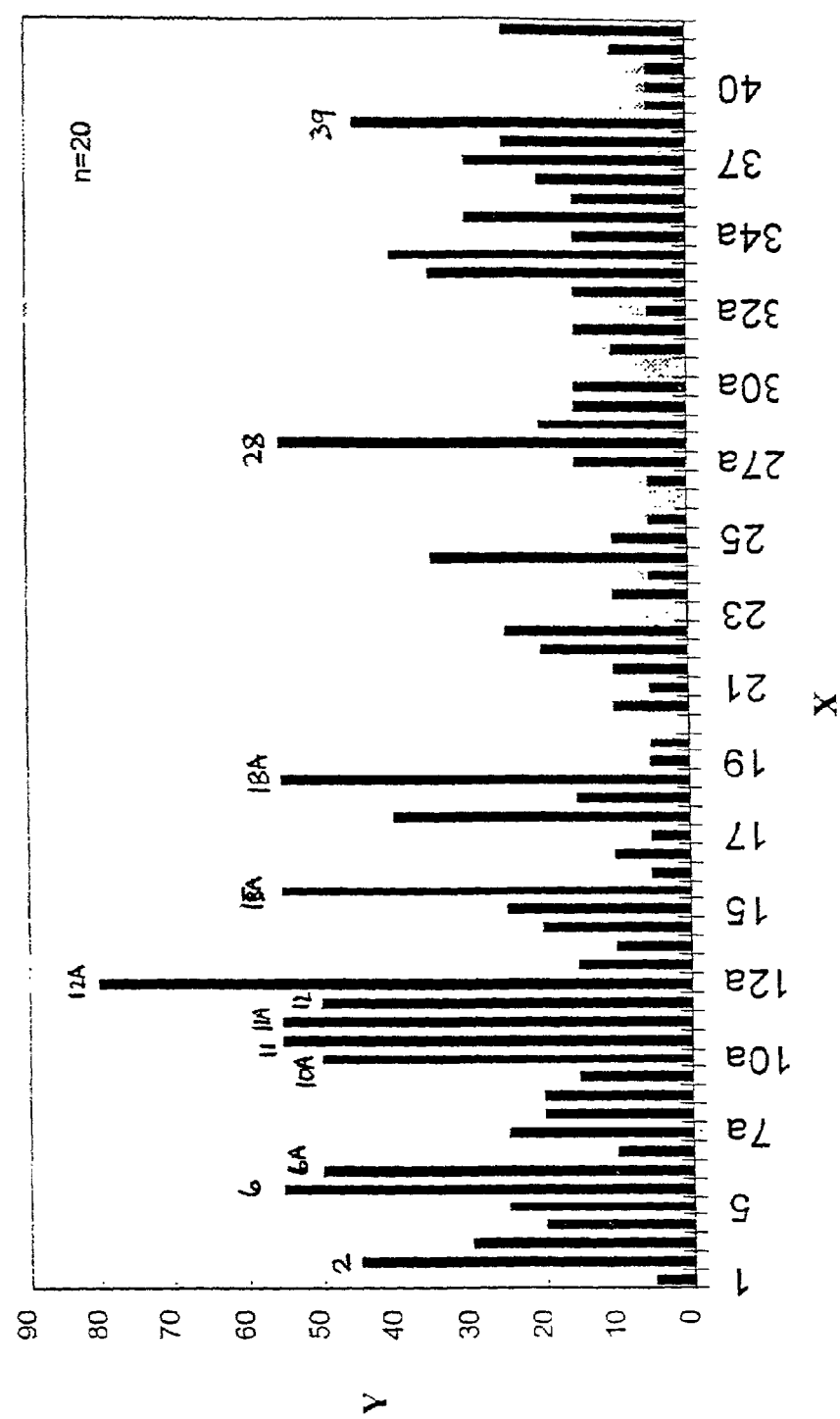
FIG. 2 shows the distribution of stimulatory RhD peptides in donors alloimmunised with RhD antigen from peptides 1 to 42 and 6A to 40A as per Tables 1, 2 and 3; x—RhD peptide added to culture; y—percentage of subjects responding to specific RhD peptides.

As shown in FIG. 2 various peptide fragments have been selected in accordance with their particular peptide sequences. These are given in Tables 1, 2 and 3 which follow and the results achieved by means of the foregoing example are shown in FIG. 2.

Accordingly we have shown that helper T-cells from all donors deliberately immunised against RhD can be stimulated in vitro by RhD peptides.

Further there is a variation between alloimmune donors in the T-cell response profile to the RhD peptides. Despite these variations, RhD peptides Nos. 2, 6, 6A, 10A, 11, 11A, 12, 12A, 15A, 18A, 28 and 39 are most commonly targeted and a proliferative response was elicited by peptide 12A in 70% of donors. However significantly related profiles are found in donors sharing HLA-DR alleles. It is predicted that alloreactive T-cell epitopes on the RhD protein would comprise sequences that are foreign to RhD-negative individuals, and would thus not be carried on the related RhCc/Ee protein that is expressed on the erythrocytes of such individuals. With the exception of peptide 28, all of the fragments identified are sequences that fulfil this prediction. It is therefore considered that such peptides, or derived sequences, could be used to stimulate either T-cell response or tolerance in vivo as desired, depending on the route of administration and/or the dose and formulation of the preparation.

The T-cells which were proliferated were in fact drawn from those that have been previously activated. This is important because it is these cells which will drive anti-D antibody production in RhD-negative donors immunised with RhD.

It follows that the characterisation of the putative helper T-cell epitopes we have identified is a key step in the development of safe immunogens for anti-immunoglobulin donors and opens the way to the evaluation of peptide immunotherapy as a novel approach to the prevention of haemolytic disease inter alia in neonates.

These experiments can be carried out using other rhesus proteins, such as RhC, Rhc, RhE or Rhe protein.

The aforementioned experiments were repeated using blood from subjects suffering from autoimmune haemolytic anaemia. It was therefore established that the T-cells of the subjects exhibited a proliferative response to peptides 2, 5, 14, 29, 31 and 38 (see FIG. 3) and 65% of patients responded to peptide 29. The results also showed a correlation between patients suffering from autoimmune haemolytic anaemia and having tissue type HLA-DR15. With the exception of peptide 31 all of the peptides are shared in common between the RhD and RhCe/Ee proteins.

EXAMPLE 2

The HLA class II tissue type of the donors tested in Example 1 was ascertained by standard SSP—PCR methods. This was carried out because the molecules that determine tissue type select and bind antigenic peptide fragments for display to T-cells therefore they are important in this investigation.

The techniques described in Barker et al (1997) Blood 90:2701-2715 were used to determine that the HLA-D loci was more important than either the HLA-DP or HLA-DQ in the presentation of Rh D peptide fragments that stimulate T-cells in vitro.

A significant proportion of Rh D-negative donors selected for responsiveness to Rh D carry the HLA-DRB1*15 gene (56% versus approx. 29% in a control population). Thus carrying this tissue type is associated with an increase risk of producing anti-D antibodies after exposure to Rh D positive erythrocytes, and there is smaller variation in HLA- DR tissue type among responders than in the general population. It has also been shown that the patterns of Rh D peptides that elicit T-cell proliferation are significantly related in Rh D-negative donors who share the same HLA-DR type (see FIGS. 3A and 3B).

For warm-type autoimmune haemolytic anaemia there is also an association with HLA DR15 with 65% of patients carrying this HLA type.

Nevertheless, a statistical analysis of all the data shows that the effect of HLA-DR type on the identity of the peptides recognised is relatively weak. In other words, many of the Rh D peptides stimulate T-cells regardless of tissue type.

These analyses demonstrate that the selection of Rh D peptide fragments for immunisation/tolerisation regimes may not be dependent on prior tissue typing of recipients, an important practical consideration for the clinical application of this approach.

EXAMPLE 3

Cultured T-cells are stimulated with each of the epitopes given in Tables 1 to 3 and after 5 days the responding cells were transferred to a flat-bottomed microtitre plates (96-well Nunc-Immuno Maxisorp) coated with 50 µl per well of monoclonal anti-cytokine capture antibody diluted in 0.05M alkaline carbonate coating buffer pH 9.6. Unbound capture antibody was removed by two washes with HBSS and non-specific binding potential blocked by incubation with 200 µl per well of phosphate buffered saline, pH 7.4 (PBS containing 3% BSA). Five days after stimulation, lymphocyte cultures were mixed to resuspend the cells and duplicate 100 µl aliquots were transferred into wells coated with the respective capture antibody specific for IFN-γ and or IL-10 or TGF-β. The plates coated with capture antibodies and layered by lymphocytes were then incubated for a further 24 hours at 37° C. in a humidified atmosphere of 5% $CO_2$ and 95% air. After this incubation the PBMC were removed by four washes with 0.2% Tween/PBS. one hundred microlitre aliquots of the appropriate biotinylated monoclonal detection antibody in 0.2% BSA/PBS were then added to the wells and incubated at room temperature for 45 minutes. After six washes with 0.5% Tween/PBS, 100 µl of 1:100,000 ExtrAvidin-alkaline phosphatase conjugate (Sigma) was then added to each of the wells and incubated at room temperature for 30 minutes. The ExtrAvidin conjugate was removed by eight washes with 0.2% Tween/PBS, and the plates developed using 100 µl per well of p-nitrophenyl phosphate (Sigma) 1.0 mg/ml in 0.05M carbonate alkaline buffer pH 9.6. The absorbence of 405 nm was then measured using a Multiscan plate reader (Labsystems Basingstoke UK).

Cytokine secretion was measured by interpolation from a standard curve generated by incubating duplicate wells with doubling dilutions of recombinant human IFN-γ or IL-10 or TGF-β (Pharmingen). The standard curves were modelled by a smoothed cubic spline function applied to the absorbence reading and the cytokine concentrations after a quasi-logarithmic transformation, where:

$$\text{quasi } \log_e(z) = \log_e[z + \sqrt{[z^2+1]}]$$

This method is very sensitive and therefore can identify that a particular Rh D peptide is capable of stimulating human T-cells to produce potentially immunosuppressive cytokines rather than to proliferate.

From FIGS. 5A and 5B it can be seen that epitopes 10, 16, 22, 24 and 34 induce IL-10 and/or TGF-β production by human T-cells. IL-10 and TGF-β molecules are known to have immunosuppressive properties. In preliminary experiments RhD peptides that induce IL-10 have been shown to inhibit T-cell proliferation in response to the entire RhD protein in vitro. Accordingly, prior administration of RhD peptides that elicit T-cell IL-10 or TGF-β production can be used to prevent RhD negative individuals from responding to RhD. It is also possible to inhibit established responses. This novel approach to manipulating the immune system has other application, including treatment of warm-type autoimmune haemolytic anaemia, in which the Rh proteins are important targets. The identification of peptides with similar properties derived from other antigens could also lead to therapy for a wide range of autoimmune diseases where the antigens/proteins are identified.

No IL-4 production was detected in any culture. In FIG. 5C it can be seen that epitopes 5, 21 and 27 stimulate IFN-γ secretion. FIG. 5D shows the level of incorporation of $^3$H-Thymidine into the T-cells after stimulation with the RhD peptides.

From FIG. 6 it can be seen that the addition of such peptides to T-cell cultures specifically blocks the proliferative response to the RhD protein, but not to a control antigen PPD. This result is very important since it raises the possibility that these peptides may also be able to inhibit damaging responses in vivo if given to patients, whilst not suppressing the rest of the immune system.

TABLE 1

| PEPTIDE NUMBER | PEPTIDE SEQUENCE | RESIDUES |
| --- | --- | --- |
| RhCE (R2 cE) | | |
| 1 | SSKYPRSVRRCLPLW | 2-16 |
| 2 | CLPLWALTLEAALIL | 12-26 |
| 3 | AALILLFYFFTHYDA | 22-36 |
| 4 | THYDASLEDQKGLVA | 32-46 |
| 5 | KGLVASYQVGQDLTV | 42-56 |
| 6 | QDLTVMAALGLGFLT | 52-66 |
| 7 | LGFLTSNFRRHSWSS | 62-76 |
| 8 | HSWSSVAFNLFMLAL | 72-86 |
| 9 | FMLALGVQWAILLDG | 82-96 |
| 10 | ILLDGFLSQFPPGKV | 92-106 |
| 11 | PPGKVVITLFSIRLA | 102-116 |
| 12 | SIRLATMSAMSVLIS | 112-126 |
| 13 | SVLISAGAVLGKVNL | 122-136 |
| 14 | GKVNLAQLVVMVLVE | 132-146 |
| 15 | MVLVEVTALGTLRMV | 142-156 |
| 16 | TLRMVISNIFNTDYH | 152-166 |
| 17 | NTDYHMNLRHFYVFA | 162-176 |
| 18 | FYVFAAYFGLTVAWC | 172-186 |
| 19 | TVAWCLPKPLPKGTE | 182-196 |
| 20 | PKGTEDNDQRATIPS | 192-206 |
| 21 | ATIPSLSAMLGALFL | 202-216 |
| 22 | GALFLWMFWPSVNSP | 212-226 |
| 23 | SVNSPLLRSPIQRKN | 222-236 |
| 24 | IQRKNAMFNTYYALA | 232-246 |
| 25 | YYALAVSVVTAISGS | 242-256 |
| 26 | AISGSSLAHPQRKIS | 252-266 |
| 27 | QRKISMTYVHSAVLA | 262-276 |
| 28 | SAVLAGGVAVGTSCH | 272-286 |
| 29 | GTSCHLIPSPWLAMV | 282-296 |
| 30 | WLAMVLGLVAGLISI | 292-306 |
| 31 | GLISIGGAKCLPVCC | 302-316 |
| 32 | LPVCCNRVLGIHHIS | 312-326 |
| 33 | IHHISVMHSIFSLLG | 322-336 |
| 34 | FSLLGLLGEITYIVL | 332-346 |
| 35 | TYIVLLVLHTVWNGN | 342-356 |
| 36 | VWNGNGMIGFQVLLS | 352-366 |
| 37 | QVLLSIGELSLAIVI | 362-376 |
| 38 | LAIVIALTSGLLTGL | 372-386 |
| 39 | LLTGLLLNLKIWKAP | 382-396 |
| 40 | IWKAPHVAKYFDDQV | 392-406 |

TABLE 1-continued

| PEPTIDE NUMBER | PEPTIDE SEQUENCE | RESIDUES |
|---|---|---|
| 41 | FDDQVFWKFPHLAVG | 402-416 |
| 42 | DDQVFWKFPHLAVGF | 403-417 |

TABLE 2

| PEPTIDE NUMBER | PEPTIDE SEQUENCE | RESIDUES |
|---|---|---|
| RhCE (R1 Ce) | | |
| 1 (C) | SSKYPRSVRRCLPLC | 2-16 |
| 2 (C) | CLPLCALTLEAALIL | 12-26 |
| 22 (e) | GALFLWMFWPSVNSA | 212-226 |
| 23 (e) | SVNSALLRSPIQRKN | 222-236 |
| RhD | | |
| 6 (also C) | QDLTVMAAIGLGFLT | 52-66 |
| 7 (also C) | LGFLTSSFRRHSWSS | 62-76 |
| 10 (also C) | ILLDGFLSQFPSGKV | 92-106 |
| 11 (also C) | PSGKVVITLFSIRLA | 102-116 |
| 12 | SIRLATMSALSVLIS | 112-126 |
| 13 | SVLISVDAVLGKVNL | 122-136 |
| 15 | MVLVEVTALGNLRMV | 142-156 |
| 16 | NLRMVISNIFNTDYH | 152-166 |
| 17 | NTDYHMNMMHIYVFA | 162-176 |
| 18 | IYVFAAYFGLSVAWC | 172-186 |
| 19 | SVAWCLPKPLPEGTE | 182-196 |
| 20 | PEGTEDKDQTATIPS | 192-206 |
| 22 | GALFLWIFWPSFNSA | 212-226 |
| 23 | SFNSALLRSPIERKN | 222-236 |
| 24 | IERKNAVFNTYYAVA | 232-246 |
| 25 | YYAVAVSVVTAISGS | 242-256 |
| 26 | AISGSSLAHPQGKIS | 252-266 |
| 27 | QGKISKTYVHSAVLA | 262-276 |
| 30 | WLAMVLGLVAGLISV | 292-306 |
| 31 | GLISVGGAKYLPGCC | 302-316 |
| 32 | LPGCCNRVLGIPHSS | 312-326 |
| 33 | IPHSSIMGYNFSLLG | 322-336 |
| 34 | FSLLGLLGEIIYIVL | 332-346 |
| 35 | IYIVLLVLDTVGAGN | 342-356 |
| 36 | VGAGNGMIGFQVLLS | 352-366 |
| 40 | IWKAPHEAKYFDDQV | 392-406 |

TABLE 3

| PEPTIDE NUMBER | PEPTIDE SEQUENCE | RESIDUES |
|---|---|---|
| RhCE (R1 Ce) | | |
| 1A (C) | RSVRRCLPLCALTLE | 7-21 |
| 22A (e) | WMFWPSVNSALLRSP | 217-231 |
| RhD | | |
| 6A (also C) | MAAIGLGFLTSSFRR | 57-71 |
| 7A (also C) | SSFRRHSWSSVAFNL | 67-81 |
| 10A (also C) | FLSQFPSGKVVITLF | 97-111 |
| 11A (also C) | VITLFSIRLATMSAL | 107-121 |
| 12A | TMSALSVLISVDAVL | 117-131 |
| 13A | VDAVLGKVNLAQLVV | 127-141 |
| 15A | VTALGNLRMVISNIF | 147-161 |
| 16A | ISNIFNTDYHMNMMH | 157-171 |
| 17A | MNMMHIYVFAAYFGL | 167-181 |
| 18A | AYFGLSVAWCLPKPL | 177-191 |
| 19A | LPKPLPEGTEDKDQT | 137-201 |
| 20A | DKDQTATIPSLSAML | 197-211 |
| 21A | LSAMLGALFLWIFWP | 207-221 |
| 22A | WIFWPSFNSALLRSP | 217-231 |
| 23A | LLRSPIERKNAVFNT | 227-241 |
| 24A | AVFNTYYAVAVSVVT | 237-251 |
| 26A | SLAHPQGKISKTYVH | 257-271 |
| 27A | KTYVHSAVLAGGVAV | 267-281 |
| 30A | LGLVAGLISVGGAKY | 297-311 |
| 31A | GGAKYLPGCCNRVLG | 307-321 |

TABLE 3-continued

| PEPTIDE NUMBER | PEPTIDE SEQUENCE | RESIDUES |
|---|---|---|
| 32A | NRVLGIPHSSIMGYN | 317-331 |
| 33A | IMGYNFSLLGLLGEI | 327-341 |
| 34A | LLGEIIYIVLLVLDT | 337-351 |
| 35A | LVLDTVGAGNGMIGF | 347-361 |
| 39A | LLNLKIWKAPHEAKY | 387-401 |
| 40A | HEAKYFDDQVFWKFP | 397-411 |

TABLE 4

| PEPTIDE NUMBER | PEPTIDE SEQUENCE | RESIDUES |
|---|---|---|
| Rh50 GP | | |
| 1 | MRFTFPLMAIVLEIA | 1-15 |
| 2 | VLEIAMIVLFGLFVE | 11-25 |
| 3 | GLFVEYETDQTVLEQ | 21-35 |
| 4 | TVLEQLNITKPTDMG | 31-45 |
| 5 | PTDMGIFFELYPLFQ | 41-55 |
| 6 | YPLFQDVHVMIFVGF | 51-65 |
| 7 | IFVGFGFLMTFLKKY | 61-75 |
| 8 | FLKKYGFSSVGINLL | 71-85 |
| 9 | GINLLVAALGLQWGT | 81-95 |
| 10 | LQWGTIVQGILQSQG | 91-105 |
| 11 | LQSQGQKFNIGIKNM | 101-115 |
| 12 | GIKNMINADFSAATV | 111-125 |
| 13 | SAATVLISFGAVLGK | 121-135 |
| 14 | AVLGKTSPTQMLIMT | 131-145 |
| 15 | MLIMTILEIVFFAHN | 141-155 |
| 16 | FFAHNEYLVSEIFKA | 151-165 |
| 17 | EIFKASDIGASMTIH | 161-175 |
| 18 | SMTIHAFGAYFGLAV | 171-185 |
| 19 | FGLAVAGILYRSGLR | 181-195 |
| 20 | RSGLRKGHENEESAY | 191-205 |
| 21 | EESAYYSDLFAMIGT | 201-215 |
| 22 | AMIGTLFLWMFWPSF | 211-225 |
| 23 | FWPSFNSAIAEPGDK | 221-235 |
| 24 | EPGDKQCRAIVDTYF | 231-245 |
| 25 | VDTYFSLAACVLTAF | 241-255 |
| 26 | VLTAFAFSSLVEHRG | 251-265 |
| 27 | VEHRGKLNMVHIQNA | 261-275 |
| 28 | HIQNATLAGGVAVGT | 271-285 |
| 29 | VAVGTCADMAIHPFG | 281-295 |
| 30 | IHPFGSMIIGSIAGM | 291-305 |
| 31 | SIAGMVSVLGYKFLT | 301-315 |
| 32 | YKFLTPLFTTKLRIH | 311-325 |
| 33 | KLRIHDTCGVHNLHG | 321-335 |
| 34 | HNLHGLPGVVGGLAG | 331-345 |
| 35 | GGLAGIVAVAMGASN | 341-355 |
| 36 | MGASNTSMAMQAAAL | 351-365 |
| 37 | QAAALGSSIGTAVVG | 361-375 |
| 38 | TAVVGGLMTGLILKL | 371-385 |
| 39 | LILKLPLWGQPSDQN | 381-395 |
| 40 | PSDQNCYDDSVYWKV | 391-405 |
| 41 | NCYDDSVYWKVPKTR | 395-409 |
| Other Peptides | | |
| BR | SKYPNCAYKTTQANKH | |
| AV2 | TIPEQSFQGSPSADT | |
| AV4 | TVKADFEFSSAPAPD | |
| AV6 | TVEERQQFGELPVSE | |
| P23 | ELKIISRCQVCMKKRH | |
| HA | PKYVKQNTLKLAT | |

The invention claimed is:

1. A method for the immunosuppression of alloimmunisation of a subject against a rhesus protein selected from the group consisting of RhD, RhC, Rhc, RhE, Rhe and Rh50 comprising administering to the subject an immunologically effective epitope of a rhesus protein selected from the group consisting of RhD, RhC, Rhc, RhE, Rhe and Rh50 protein.

2. A method for the immunosuppression of a response elicited by alloimmunisation of a subject against a rhesus protein selected from the group consisting of RhD, RhC, Rhc, RhE, Rhe and Rh50 comprising administering to the subject an immunologically effective epitope of a rhesus protein selected from the group consisting of RhD, Rhc, Rhc, RhE, Rhe and Rh50 protein.

3. A method according to claim 1 or 2 wherein the epitope is selected from at least one of SEQ ID numbers 2, 5, 6, 11, 12, 14, 28, 29, 31, 38, 39, 44, 47, 50, 51, 66, 75, 77, 78, 79, 81 and 84.

4. A method according to claim 3 wherein the epitope is SEQ ID No:79.

5. A method according to claim 1 or 2 wherein the epitope is artificially synthesised.

6. A method of claim 1 or 2 wherein the epitope is disposed in a pharmacologically acceptable vehicle.

7. A method according to claim 6 wherein the vehicle is selected such that the composition is in an injectable, oral, rectal, topical or spray-uptake form.

8. A method according to claim 6 wherein the pharmaceutically acceptable vehicle is adapted for transdermal or transmucosal administration or wherein said vehicle is a formulation with an enteric coating for oral administration.

9. A method for the tolerisation of a patient who may become alloimmunised against a rhesus protein selected from the group consisting of RhD, RhC, Rhc, RhE, Rhe and Rh50 comprising administering an epitope selected from a RhD, RhC, Rhc, RhE, Rhe or Rh50 protein or selected from at least one of SEQ ID numbers 2, 5, 6, 11, 11A, 12, 14, 28, 29, 31, 38, 39, 44, 47, 50, 51, 66, 75, 77, 78, 79, 81 and 84, and a pharmaceutically acceptable vehicle therefor.

10. A method for the immunosuppression of an alloimmunised patient against a rhesus protein selected from the group consisting of RhD, RhC, Rhc, RhE, Rhe and Rh50 comprising administering an epitope selected from a RhD, RhC, Rhc, RhE, Rhe or Rh50 protein or selected from at least one of SEQ ID numbers 2, 5, 6, 11, 11A, 12, 14, 28, 29, 31, 38, 39, 44, 47, 50, 51, 66, 75, 77, 78, 79, 81 and 84, and a pharmaceutically acceptable vehicle therefor.

11. A method according to either claim 9 or 10 wherein the vehicle is adapted for transdermal or transmucosal administration.

* * * * *

UNITED STATES PATENT AND TRADEMARK OFFICE
CERTIFICATE OF CORRECTION

PATENT NO. : 7,285,524 B1 Page 1 of 1
APPLICATION NO. : 09/857097
DATED : October 23, 2007
INVENTOR(S) : Urbaniak et al.

It is certified that error appears in the above-identified patent and that said Letters Patent is hereby corrected as shown below:

In column 3, line 20: Please delete "can used during subsequent preg." And insert --can be used during subsequent preg.--.

In column 7, line 35: Please delete "10041 volumes" and insert --100μl volumes--.

In column 9, line 39: Please delete "one hundred" and insert --One hundred--.

In column 73, lines 13-14 in claim 2: Please delete "Rhc, Rhc" and insert --RhC, Rhc--.

Signed and Sealed this

Thirtieth Day of September, 2008

JON W. DUDAS
*Director of the United States Patent and Trademark Office*